United States Patent
Retailleau et al.

(10) Patent No.: US 11,845,874 B2
(45) Date of Patent: *Dec. 19, 2023

(54) RADIATION CURABLE INKJET INKS FOR INTERIOR DECORATION

(71) Applicant: AGFA NV, Mortsel (BE)

(72) Inventors: Matthieu Retailleau, Mortsel (BE); Johan Loccufier, Mortsel (BE); An Vankeerberghen, Mortsel (BE)

(73) Assignee: AGFA NV, Mortsel (BE)

( * ) Notice: Subject to any disclaimer, the term of this patent is extended or adjusted under 35 U.S.C. 154(b) by 245 days.

This patent is subject to a terminal disclaimer.

(21) Appl. No.: 17/425,184

(22) PCT Filed: Jan. 17, 2020

(86) PCT No.: PCT/EP2020/051089
§ 371 (c)(1),
(2) Date: Jul. 22, 2021

(87) PCT Pub. No.: WO2020/152037
PCT Pub. Date: Jul. 30, 2020

(65) Prior Publication Data
US 2022/0119662 A1    Apr. 21, 2022

(30) Foreign Application Priority Data

Jan. 24, 2019   (EP) ..................... 19153561

(51) Int. Cl.
| C09D 11/38 | (2014.01) |
| C08F 220/28 | (2006.01) |
| B41J 11/00 | (2006.01) |
| C08F 2/50 | (2006.01) |
| C08F 226/06 | (2006.01) |
| C08K 5/36 | (2006.01) |

(52) U.S. Cl.
CPC ......... *C09D 11/38* (2013.01); *B41J 11/00214* (2021.01); *C08F 2/50* (2013.01); *C08F 220/286* (2020.02); *C08F 226/06* (2013.01); *C08K 5/36* (2013.01)

(58) Field of Classification Search
None
See application file for complete search history.

(56) References Cited

U.S. PATENT DOCUMENTS

| 2003/0083396 A1 | 5/2003 | Ylitalo et al. |
| 2010/0240825 A1 | 9/2010 | Shimohara |
| 2012/0113201 A1 | 5/2012 | Kagose et al. |
| 2015/0191627 A1 | 7/2015 | Illsley et al. |
| 2022/0119656 A1* | 4/2022 | Loccufier ............... C09D 11/38 |

FOREIGN PATENT DOCUMENTS

| EP | 2053101 A1 | 4/2009 |
| EP | 2093265 A1 | 8/2009 |
| JP | 2007045853 A * | 2/2007 |
| JP | 2010-18739 A | 1/2010 |
| WO | WO 2017/205609 A1 | 11/2017 |
| WO | WO 2017/211587 A1 | 12/2017 |

OTHER PUBLICATIONS

European Patent Office, International Search Report in International Patent Application No. PCT/EP2020/051089, 4 pp. (Mar. 27, 2020).
European Patent Office, Written Opinion in International Patent Application No. PCT/EP2020/051089, 6 pp. (Mar. 27, 2020).

* cited by examiner

*Primary Examiner* — Sanza L. McClendon
(74) *Attorney, Agent, or Firm* — Leydig, Voit & Mayer, Ltd.

(57) ABSTRACT

A radiation curable inkjet ink containing at least one or two compounds selected from the group consisting of a polymerizable compound including a vinylether group or a vinylamide group, an amine synergist including an alkanolamine group or a dimethyl benzoate group, and a Norrish Type II photoinitiator including a photoinitiating moiety selected from the group consisting of a thioxanthone group, a benzophenone group, a ketocoumarin group and a camphorquinone group; and a singlet oxygen quencher including at least one specific amino-thioether group.

18 Claims, No Drawings

RADIATION CURABLE INKJET INKS FOR INTERIOR DECORATION

CROSS-REFERENCE TO RELATED APPLICATIONS

This patent application is a U.S. National Phase application of International Patent Application No. PCT/EP2020/051089, filed Jan. 17, 2020, which claims the benefit of European Patent Application No. 19153561.6, filed Jan. 24, 2019.

TECHNICAL FIELD

The present invention relates to radiation curable inkjet inks, especially UV curable inkjet inks for manufacturing decorative articles for indoor decoration.

BACKGROUND

Due to their enhanced reliability, inkjet printing systems are incorporated into industrial production lines. The main advantage of inkjet is that it offers high flexibility, such as variable data printing allowing small run lengths or even a single print without large pre-print preparations. Radiation curable inkjet inks are particularly preferred because high quality images can also be printed on non-absorbing ink-receivers, especially when the inkjet inks contain no or small amounts of volatile organic solvents or water.

A typical property of an inkjet ink is that it must have a very low viscosity, e.g. 5 to 15 mPa·s at printing temperature, in order to be jettable in small droplets having a volume in the picoliter range. To reach these low viscosity values, radiation curable inks must contain very high levels of reactive diluent. These reactive diluents having low viscosity often exhibit low radiation curing reactivity and bad smell, which can further be accompanied with irritation problems. The latter is unacceptable for interior decoration, where health risks and bad smell must be minimized.

So-called low migration radiation curable inkjet inks have been designed for food packaging applications. For example, EP 2053101 A (AGFA) discloses curable inkjet inks that have very low amounts of extractable monomers and photoinitiators by using hybrid monomers having two different types of polymerizable groups, such as an acrylate group and a vinylether group. However, it was observed, that although vinylether compounds are very effective at reducing the viscosity of inkjet inks, under certain conditions they easily hydrolyse to generate a strong and unpleasant odour.

One approach to reduce bad smell is to combine the vinylether acrylate monomers with specific monomers. For example, US 2012113201 (SEIKO EPSON) discloses in [0155] that in order to reduce the viscosity and a bad odour, at least one of phenoxyethyl (meth)acrylate and isobornyl (meth)acrylate is used, with the phenoxyethyl (meth)acrylate being more preferred.

WO 2017/205609 A (EFI) discloses low odor radiation curable inks comprising: 10-40% w/w of 4-hydrobutylacrylate, 5-25% of a urethane (math)acrylate oligomer, 10-55% of diacrylates, one or more photoinitiators, one or more additives, and one or more pigments; wherein the ink composition contains less than 1% of monofunctional monomers that have an undesired odor selected from the group consisting of: vinyl caprolactam, 2-phenoxyethyl acrylate, isodecyl acrylate, 3,3,5-trimethylcyclohexyl acrylate, isooctyl acrylate, octyldecyl acrylate, isobornyl acrylate, cycloaliphatic acrylate monomer, benzyl acrylate, di(ethylene glycol) 2-ethylhexyl acrylate, tridecyl acrylate, 2(2-ethoxyethoxy)ethyl acrylate, lauryl acrylate, tetrahydrofurfuryl acrylate, and any combination thereof.

Instead of volatile monomers, bad odour may also be the result of the formation of aldehydes from other compounds upon UV curing. Furthermore, certain aldehydes have also been linked to health risks, such as formaldehyde that has been associated with excess risk of nasopharyngeal and other cancers. Hence, another approach is to include hydrolysis stabilizers. For example, US 20030083396 A (3 M) discloses the use of carbodiimide compounds, such as Staboxol™ I from Rhein Chemie Corporation, in radiation curable inkjet inks. However, it was found that these commercial compounds do not work well in all circumstances.

Another approach is given by US 2015191627 A (SUN CHEMICAL) wherein the printed radiation curable inks are coated with a solvent- or water-based overprint varnish to reduce the level of odorous species which would otherwise emanate from a printed substrate. However, such an approach complicates the design of an inkjet printer.

Hence, there still remains a need for radiation curable inkjet inks, especially UV curable inkjet inks for interior decoration applications, exhibiting low odour and health risks caused by aldehydes.

SUMMARY OF INVENTION

In order to overcome the problems described above, preferred embodiments of the present invention have been realized with a radiation curable inkjet ink as defined in claim 1.

Like many sulfur-containing compounds, thioethers are generally associated with causing foul odours. It was surprisingly found that certain compounds having one or more specific amino-thioether groups were capable of reducing bad smell and health risks caused by aldehydes upon UV exposure of layers made from radiation curable inkjet inks containing polymerizable vinylether compounds or certain Norrish Type II photoinitiators. It is believed that these specific aminothioether compounds function as singlet oxygen quenchers.

These and other objectives will become apparent from the detailed description hereinafter.

DESCRIPTION OF EMBODIMENTS

Definitions

The term "radiation curable", as used in radiation curable inkjet ink means that the inkjet ink is curable by actinic radiation, such as UV radiation and e-beam, preferably UV radiation. The latter inkjet inks are also referred to as UV curable inkjet inks.

The term "monofunctional", as used in monofunctional polymerizable compounds means polymerizable compounds containing a single polymerizable group.

The term "polyfunctional", as used in polyfunctional polymerizable compounds means polymerizable compounds containing two, three or more polymerizable groups.

The term "alkyl" means all variants possible for each number of carbon atoms in the alkyl group i.e. methyl, ethyl, for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methyl-butyl, etc. This applies in a similar manner also to alkenyl, alkynyl, alkaryl and aralkyl groups.

The term "substituted", in e.g. substituted alkyl group means that the alkyl group may be substituted by other atoms than the atoms normally present in such a group, i.e. carbon and hydrogen. For example, a substituted alkyl group may include a halogen atom or a thiol group. An unsubstituted alkyl group contains only carbon and hydrogen atoms.

Unless otherwise specified a substituted alkyl group, a substituted alkenyl group, a substituted alkynyl group, a substituted aralkyl group, a substituted alkaryl group, a substituted aryl and a substituted heteroaryl group are preferably substituted by one or more constituents selected from the group consisting of ester, amide, ether, thioether, ketone, aldehyde, sulfoxide, sulfone, sulfonate ester, sulphonamide, —Cl, —Br, —I, —OH, —SH, —CN and —NO$_2$.

Unless otherwise specified a substituted or unsubstituted alkyl group is preferably a $C_1$ to $C_6$-alkyl group.

Unless otherwise specified a substituted or unsubstituted alkenyl group is preferably a $C_2$ to $C_6$-alkenyl group.

Unless otherwise specified a substituted or unsubstituted alkynyl group is preferably a $C_2$ to $C_6$-alkynyl group.

Unless otherwise specified a substituted or unsubstituted aralkyl group is preferably a phenyl or naphthyl group including one, two, three or more $C_1$ to $C_6$-alkyl groups.

Unless otherwise specified a substituted or unsubstituted alkaryl group is preferably a $C_7$ to $C_{25}$-alkyl group including a phenyl group or a naphthyl group.

A cyclic group includes at least one ring structure and may be a monocyclic- or polycyclic group, the latter meaning one or more rings fused together.

A heterocyclic group is a cyclic group that has atoms of at least two different elements as members of its ring(s). The counterparts of heterocyclic groups are homocyclic groups, the ring structures of which are made of carbon only. Unless otherwise specified a substituted or unsubstituted heterocyclic group is preferably a five- or six-membered ring substituted by one, two, three or four heteroatoms, preferably selected from oxygen atoms, nitrogen atoms, sulfur atoms, selenium atoms or combinations thereof.

An alicyclic group is a non-aromatic homocyclic group wherein the ring atoms consist of carbon atoms.

The term heteroaryl group means a monocyclic- or polycyclic aromatic ring comprising carbon atoms and one or more heteroatoms in the ring structure, preferably, 1 to 4 heteroatoms, independently selected from nitrogen, oxygen, selenium and sulphur. Preferred examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, isoxazolyl, and oxazolyl. A heteroaryl group can be unsubstituted or substituted with one, two or more suitable substituents. Preferably, a heteroaryl group is a monocyclic ring, wherein the ring comprises 1 to 5 carbon atoms and 1 to 4 heteroatoms. More preferably a substituted or unsubstituted heteroaryl group is preferably a five- or six-membered ring substituted by one, two or three oxygen atoms, nitrogen atoms, sulphur atoms, selenium atoms or combinations thereof.

Unless otherwise specified an unsubstituted aryl group is preferably a phenyl group or naphthyl group.

Unless otherwise specified an acyl group is preferably a —C(=O)—R group wherein R is selected from the group consisting of an optionally substituted alkyl group, an optionally substituted aryl group, an optionally substituted heteroaryl group, an optionally substituted alkenyl group, an optionally substituted alkynyl group, an optionally substituted alkaryl group and an optionally substituted aralkyl group.

The acyl group in the present invention is preferably a benzoyl group such as a 2,6-dimethyl benzoyl group, a 2,6-dimethoxy benzoyl group or a 2,4,6-trimethyl benzoyl group.

Radiation Curable Inkjet Inks

In a preferred embodiment of the invention, the radiation curable inkjet ink includes a) at least one or two compounds selected from the group consisting of a polymerizable compound including a vinylether group or a vinylamide group, an amine synergist including an alkanolamine group or a dimethyl benzoate group, and a Norrish Type II photoinitiator including a photoinitiating moiety selected from the group consisting of a thioxanthone group, a benzophenone group, a ketocoumarin group and a camphorquinone group, preferably a thioxanthone group and a benzophenone group, and more preferably a thioxanthone group; and b) a singlet oxygen quencher including at least one amino-thioether group according to Formula (I):

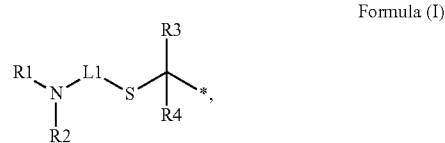

Formula (I)

wherein
* represents the point of attachment in the singlet oxygen quencher;

$L_1$ represents a divalent linking group positioning S and N in a 1 to 2 to a 1 to 4 position;

$R_1$ and $R_2$ are independently selected from the group consisting of a $C_1$-$C_6$-alkyl group, a $C_2$-$C_6$-alkenyl group, $C_2$-$C_6$-alkynyl group and a $C_7$-$C_{12}$-aralkyl group, wherein any of said $C_1$-$C_6$-alkyl group, $C_2$-$C_6$-alkenyl group, a $C_2$-$C_6$-alkynyl group and $C_7$-$C_{12}$-aralkyl group may be interrupted by at least one heteroatom selected from the group consisting of a nitrogen, an oxygen and a sulphur; and is optionally functionalized with a functional group selected from the group consisting of an ester, an amide, a ketone, an aldehyde, a sulfone, a sulfonate ester and a phosphonate;

$R_3$ and $R_4$ are independently selected from the group consisting of a hydrogen, a $C_1$-$C_6$-alkyl group, a $C_2$-$C_6$-alkynyl group, a $C_7$-$C_{12}$-aralkyl group and an electron withdrawing group selected from the group consisting of an ester, an amide, a ketone and an aldehyde; and any of $R_1$, $R_2$, $R_3$, $R_4$, N and L1 may represent the necessary atoms to form a five to eight membered ring.

In a more preferred embodiment, $R_3$ and $R_4$ represent a hydrogen. In a further preferred embodiment, $L_1$ is selected from the group consisting of an ethylene group, a propylene group and a butylene group.

In a more preferred embodiment of the invention, the radiation curable inkjet ink contains a) a polymerizable compound including a vinylether group and/or a Norrish Type II photoinitiator including a photoinitiating moiety selected from the group consisting of a thioxanthone group and a benzophenone group; and b) a singlet oxygen quencher including at least one amino-thioether group according to Formula (I):

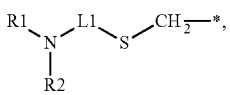

Formula (II)

wherein
* represents the point of attachment in the singlet oxygen quencher;
L1 represents a divalent linking group positioning S and N in a 1 to 2 to a 1 to 4 position; R1 and R2 are independently selected from the group consisting of a $C_1$-$C_6$-alkyl group, a $C_2$-$C_6$-alkyl group which is interrupted by one oxygen atom and/or an ester group, a $C_2$-$C_6$-alkenyl group, a $C_2$-$C_6$-alkenyl group which is interrupted by one oxygen atom and/or an ester group, a $C_2$-$C_6$-alkynyl group, a $C_2$-$C_6$-alkynyl group which is interrupted by one oxygen atom and/or an ester group, a $C_7$-$C_{12}$-aralkyl group; or any of
R1, R2, N and L1 may represent the necessary atoms to form a five to eight membered ring.

The radiation curable inkjet ink may be a colourless radiation curable inkjet ink, but preferably it contains a colorant. Colourless radiation curable inkjet inks may be used, for example, as a primer to improve adhesion to substrate, or as a varnish to improve the glossiness of an image.

For printing multi-colour images, the radiation curable inkjet ink is part of a radiation curable inkjet ink set. A preferred radiation curable inkjet ink set for printing different colours contains at least two or three but most preferably at least four radiation curable inkjet inks in accordance with the invention. The inkjet ink set is preferably a radiation curable CMYK or CRYK inkjet ink set, preferably further including a radiation curable white inkjet ink for enhancing colour vibrancy. This inkjet ink set may also be extended with extra inks such as violet, green, red, blue, and/or orange to further enlarge the colour gamut of the image. The radiation curable inkjet ink set may also be extended by the combination of full density inkjet inks with light density inkjet inks. The combination of dark and light colour inks and/or black and grey inks improves the image quality by a lowered graininess.

In a preferred embodiment, the radiation curable inkjet ink contains an organic colour pigment preferably in an amount of 0.1 to 13.0 wt %, more preferably 1.0 to 10.0 wt % and most preferably 2.0 to 8.0 wt based on the total weight of the radiation curable inkjet ink. In the above ranges the colour gamut is maximized.

For light density colour inkjet inks, the organic colour pigment is preferably present in an amount of 0.1 to 1.0 wt %, preferably 0.2 to 0.9 wt %, more preferably 0.3 to 0.5 wt %, based on the total weight of the radiation curable inkjet ink. In the above ranges the graininess in a printed image is minimized.

The radiation curable inkjet ink preferably includes 60 to 95 wt % of polymerizable compounds, more preferably 70 to 90 wt % of polymerizable compounds based upon the total weight of the radiation curable inkjet ink. A varnish may include up to 99 wt % of polymerizable compounds based upon the total weight of the radiation curable inkjet ink.

For having a good ejecting ability, the viscosity of the radiation curable inkjet ink at the jetting temperature is preferably smaller than 30.0 mPa·s, more preferably smaller than 20.0 mPa·s, most preferably between 5.0 and 16.0 mPa·s or even between 8.0 and 15.0 mPa·s at a shear rate of 1000 $s^{-1}$ and a jetting temperature between 30 and 70° C., preferably at a temperature of 45° C.

The surface tension of the radiation curable inkjet ink is preferably in the range of 20 mN/m to 35 mN/m at 25° C., more preferably in the range of about 22 mN/m to about 30 mN/m at 25° C. In these ranges, good ink spreading is obtained on a wide range of substrates.

The radiation curable inkjet ink may further also contain at least one polymerization inhibitor for improving the thermal stability of the ink.

The radiation curable inkjet ink may further also contain at least one surfactant for obtaining good spreading characteristics on a substrate.

There is no limitation in combining any of the above preferred embodiments with each other.

Singlet Oxygen Quenchers

The singlet oxygen quencher includes at least one amino-thioether group according to Formula (I):

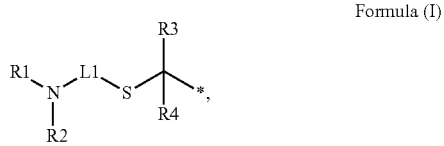

Formula (I)

wherein
* represents the point of attachment in the singlet oxygen quencher;
$L_1$ represents a divalent linking group positioning S and N in a 1 to 2 to a 1 to 4 position;
R1 and R2 are independently selected from the group consisting of a $C_1$-$C_6$-alkyl group, a $C_2$-$C_6$-alkenyl group, a $C_2$-$C_6$-alkynyl group and a $C_7$-$C_{12}$-aralkyl group, wherein any of said $C_1$-$C_6$-alkyl group, $C_2$-$C_6$-alkenyl group, a $C_2$-$C_6$-alkynyl group and $C_7$-$C_{12}$-aralkyl group may be interrupted by at least one heteroatom selected from the group consisting of a nitrogen, an oxygen and a sulphur; and is optionally functionalized with a functional group selected from the group consisting of an ester group, an amide group, a ketone group, an aldehyde group, a sulfone group, a sulfonate ester group and a phosphonate group;
$R_3$ and $R_4$ are independently selected from the group consisting of a hydrogen, a $C_1$-$C_6$-alkyl group, a $C_2$-$C_6$-alkenyl group, a $C_2$-$C_6$-alkynyl group, a $C_7$-$C_{12}$-aralkyl group and an electron withdrawing group selected from the group consisting of an ester group, an amide group, a ketone group and an aldehyde group; and
any of R1, R2, R3, R4, N and L1 may represent the necessary atoms to form a five to eight membered ring.

In a more preferred embodiment, R3 and R4 represent a hydrogen. In a further preferred embodiment, L1 is selected from the group consisting of an ethylene group, a propylene group and a butylene group.

In a more preferred embodiment, the singlet oxygen quencher includes at least one amino-thioether group according to Formula (II):

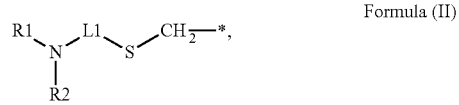

Formula (II)

wherein
* represents the point of attachment in the singlet oxygen quencher;

L1 represents a divalent linking group positioning X and N in a 1 to 2 to a 1 to 4 position; R1 and R2 are independently selected from the group consisting of a $C_1$-$C_6$-alkyl group, a $C_2$-$C_6$-alkyl group which is interrupted by one oxygen atom and/or an ester group, a $C_2$-$C_6$-alkenyl group, a $C_2$-$C_6$-alkenyl group which is interrupted by one oxygen atom and/or an ester group, a $C_2$-$C_6$-alkynyl group, a $C_2$-$C_6$-alkynyl group which is interrupted by one oxygen atom and/or an ester group, a $C_7$-$C_{12}$-aralkyl group; or any of R1, R2, S and L1 may represent the necessary atoms to form a five to eight membered ring. In a further preferred embodiment, L1 represents a substituted or unsubstituted ethylene group, a substituted or unsubstituted propylene group and substituted or unsubstituted butylene group, an ethylene group and a propylene group being more preferred, an ethylene group being the most preferred.

$R_1$ and R2 in formula (I) and (II) preferably represent a $C_2$ to $C_6$ alkyl group.

In another preferred embodiment, the singlet oxygen quencher is a difunctional singlet oxygen quencher, meaning that it comprises at least two structural moieties according to Formula (I).

The singlet oxygen quencher preferably has a molecular weight of at least 200, more preferably at least 400 and most preferably at least 600. Such a minimum molecular weight minimizes the volatility of the singlet oxygen quencher.

The singlet oxygen quencher preferably has a molecular weight of at most 20,000, more preferably at most 10,000 and most preferably at most 5,000. Such a maximum molecular weight minimizes the viscosity increase of the radiation curable inkjet ink. For a polymeric singlet oxygen quencher, the molecular weight is the Weight Average Molecular Weight.

Instead of a polymeric singlet oxygen quencher, preferably a polymerizable singlet oxygen quencher is used. So the singlet oxygen quencher including at least one amino-thioether group according to Formula (I) is preferably further functionalized with at least one free radical polymerizable functional group, preferably selected from the group consisting of an acrylate, a methacrylate, an acrylamide and a methacrylamide, an acrylate and a methacrylate being more preferred, an acrylate being the most preferred. The presence of a polymerizable group reduces the volatility of the amino-thioether compound, especially when it has a molecular weight below 300 or 400.

The singlet oxygen quencher is preferably present in the inkjet ink in an amount of 1.0 to 20.0 wt %, more preferably 2.0 to 10.0 wt % and most preferably 2.5 to 7.0 wt % based on the total weight of the inkjet ink.

The effects of reduced health risks and bad smell are obtained as long as the singlet oxygen quencher contains at least one amino-thioether group. Hence, the single oxygen quencher may have quite different chemical structures. As an illustration a number of preferred chemical structures are disclosed here below.

In another preferred embodiment, said singlet oxygen quencher comprises at least on amino-thioether according to Formula (III):

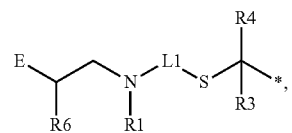

Formula (III)

wherein E is selected from the group consisting of an ester group and an amide group;

R6 is selected from the group consisting of a hydrogen and a methyl group;

R1, L1, R3 and R4 are defined as above for Formula (I) or (II).

In a more preferred embodiment, E represents an ester group and R6 represents a hydrogen. In an even more preferred embodiment, R3 and R4 represent a hydrogen.

So-called monofunctional singlet oxygen quenchers containing one amino-thioether group according to Formula (I) are preferably represented by a compound according to Formula (IV):

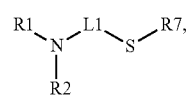

Formula (IV)

wherein R1, R2 and L1 are defined as above for Formula (I) or (II); R7 is selected from the group consisting of a methyl group, $C_2$-$C_{20}$-alkyl group, a $C_2$-$C_{20}$-alkenyl group, a $C_2$-$C_{20}$-alkynyl group and a $C_7$-$C_{20}$-aralkyl group, wherein any of said $C_2$-$C_{20}$-alkyl group, $C_2$-$C_{20}$-alkenyl group, $C_2$-$C_{20}$-alkynyl group and $C_7$-$C_{20}$-aralkyl group may be interrupted by at least one hetero-atom selected from the group consisting of a nitrogen, an oxygen and a sulphur or may be optionally functionalized with a functional group selected from the group consisting of an ester group, an amide group, a ketone group, an aldehyde group, a sulfone group, a sulfonate ester group and a phosphonate group.

In a particularly preferred embodiment, R7 is selected from the group consisting of a oligomeric ether selected from ethylene oxide, propylene oxide and tetramethylene oxide or combinations thereof, and a —$CH_2CHR_9E$ group, wherein E is selected from the group consisting of an ester group or an amide group and $R_9$ represents a hydrogen or a methyl group.

In a particularly preferred embodiment the monofunctional singlet oxygen quenchers containing one amino-thioether group according to Formula (I) are preferably represented by a compound according to Formula (V):

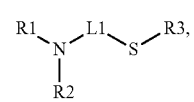

Formula (V)

wherein R1, R2 and L1 have the same meaning as for the singlet oxygen quencher according to Formula (I); and R3 represents a group selected from the group consisting of a $C_1$-$C_{20}$-alkyl group, a $C_2$-$C_{20}$-alkyl group which is interrupted by one oxygen atom and/or an ester group, a $C_2$-$C_{20}$-alkenyl group, a $C_2$-$C_{20}$-alkenyl group which is interrupted by one or more oxygen atoms and/or ester groups, a $C_2$-$C_{20}$-alkynyl group, a $C_2$-$C_{20}$-alkynyl group which is interrupted by one or more oxygen atom and/or ester groups, a $C_7$-$C_{20}$-aralkyl group, and one or more free radical polymerizable functional groups selected from the group consisting of an acrylate, a methacrylate, an acrylamide and a methacrylamide. For the one or more free radical polymerizable functional groups, an acrylate and a methacrylate being more preferred, an acrylate being the most preferred.

In another preferred embodiment said singlet oxygen quencher comprises at least on amino-thioether according to Formula (VI):

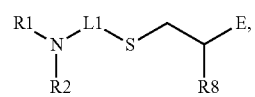

Formula (VI)

wherein

E is selected from the group consisting of an ester group and an amide group; R8 is selected from the group consisting of a hydrogen and a methyl group; R1, R2 and L1 are defined as above for Formula (I) or (II).

In a more preferred embodiment, E represents an ester group and R8 represents a hydrogen.

Particularly preferred examples of such monofunctional singlet oxygen quenchers include the compounds SOQ-1 to SOQ-15:

SOQ-1

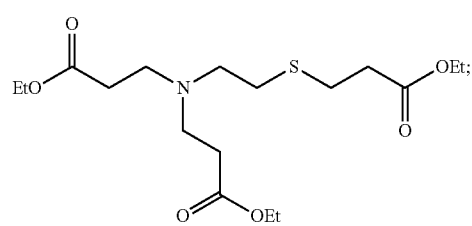

SOQ-2

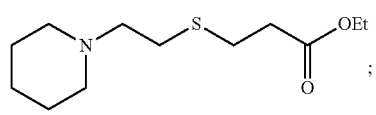

SOQ-3

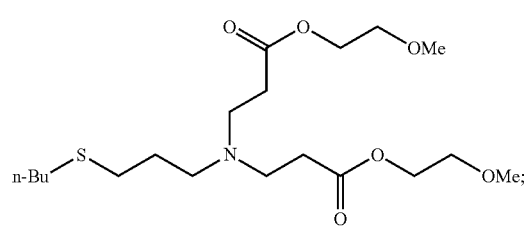

SOQ-4

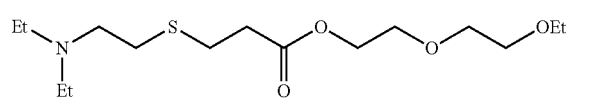

SOQ-5

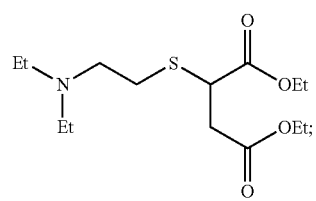

SOQ-6

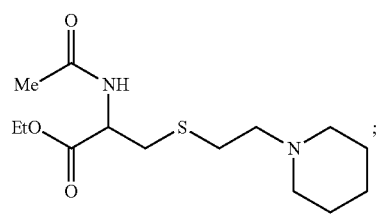

SOQ-7

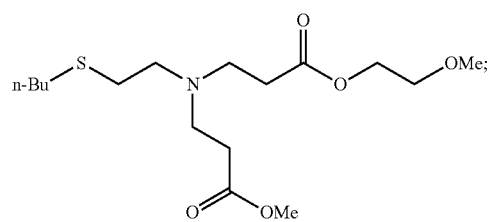

SOQ-8

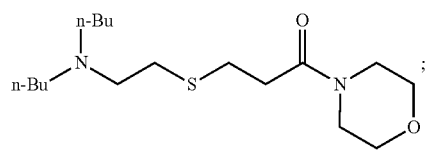

SOQ-9

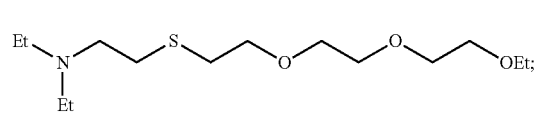

SOQ-10

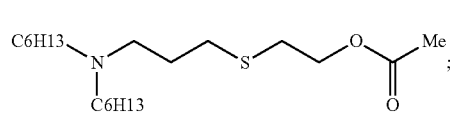

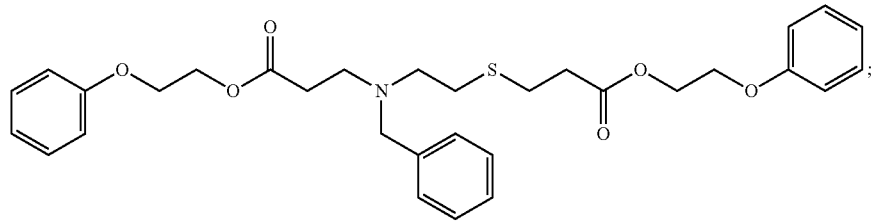

SOQ-11

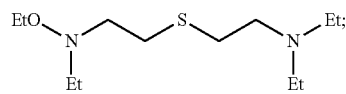

SOQ-12

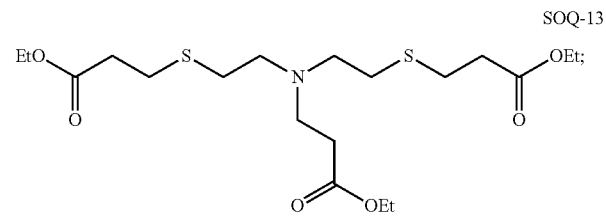

SOQ-13

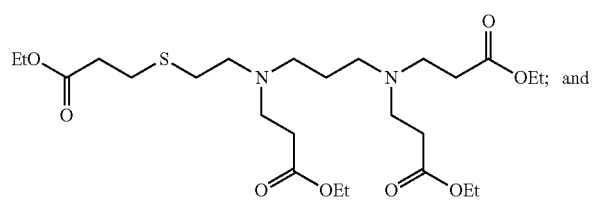

SOQ-14

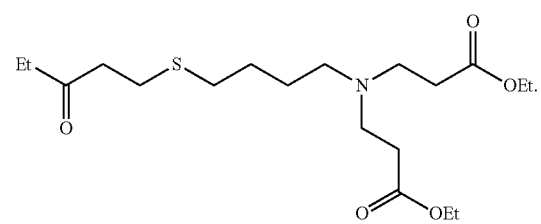

SOQ-15

Alternatively, a so-called polyfunctional singlet oxygen quencher may be used. Such compounds have two, three or more amino-thioether groups according to Formula (I), which may be identical or different.

Duofunctional singlet oxygen quenchers, i.e. polyfunctional singlet oxygen quenchers having two amino-thioether groups according to Formula (I), are preferably represented by Formula (VII):

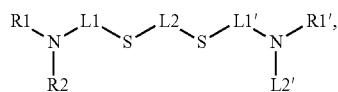

Formula (VII)

wherein
L1 and L1' independently represent a divalent linking group positioning S and N in a 1 to 2 to a 1 to 4 position; R1, R2, R1' and R2' are independently selected from the group consisting of a $C_1$-$C_6$-alkyl group, a $C_2$-$C_6$-alkenyl group, a $C_2$-$C_6$-alkynyl group and a $C_7$-$C_{12}$-aralkyl group wherein any of the $C_1$-$C_6$-alkyl group, the $C_2$-$C_6$-alkenyl group, the $C_2$-$C_6$-alkynyl group and the $C_7$-$C_{12}$-aralkyl group may be interrupted by at least one hetero-atom selected from the group consisting of a nitrogen, an oxygen and a sulphur, or may be optionally functionalized with a functional group selected from the group consisting of an ester group, an amide group, a ketone group, an aldehyde group, a sulfone group, a sulfonate ester group and a phosphonate group; L2 represents a divalent linking group selected from the group consisting of an alkylene group, an alkenylene group, an alkynylene group, an aralkylene group, all of them comprising no more than 20 carbon atoms and optionally interrupted by a hetero-atom selected from the group of an oxygen, a sulphur or a nitrogen and/or a functional group selected from the group consisting of an ester group, an amide group, and an oligo-ether group selected from the group consisting of an oligo-ethylene oxide, an oligo-propylene oxide and an oligo-tetramethylene oxide or combinations thereof.

In a preferred embodiment of the duofunctional singlet oxygen quencher according to Formula (1b), R1, R2 and L1 are identical to respectively R1', R2' and L1'.

In a preferred embodiment, L1 and L1' represents a substituted or unsubstituted ethylene group, a substituted or unsubstituted propylene group and substituted or unsubstituted butylene group, an ethylene group and a propylene group being more preferred, an ethylene group being the most preferred.

Particularly preferred examples of such polyfunctional singlet oxygen quenchers include the compounds MSOQ-1 to MSOQ-13:

MSOQ-1

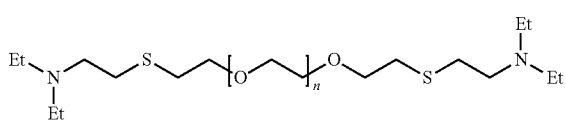

with n representing an integer of 2 to 20 on average;

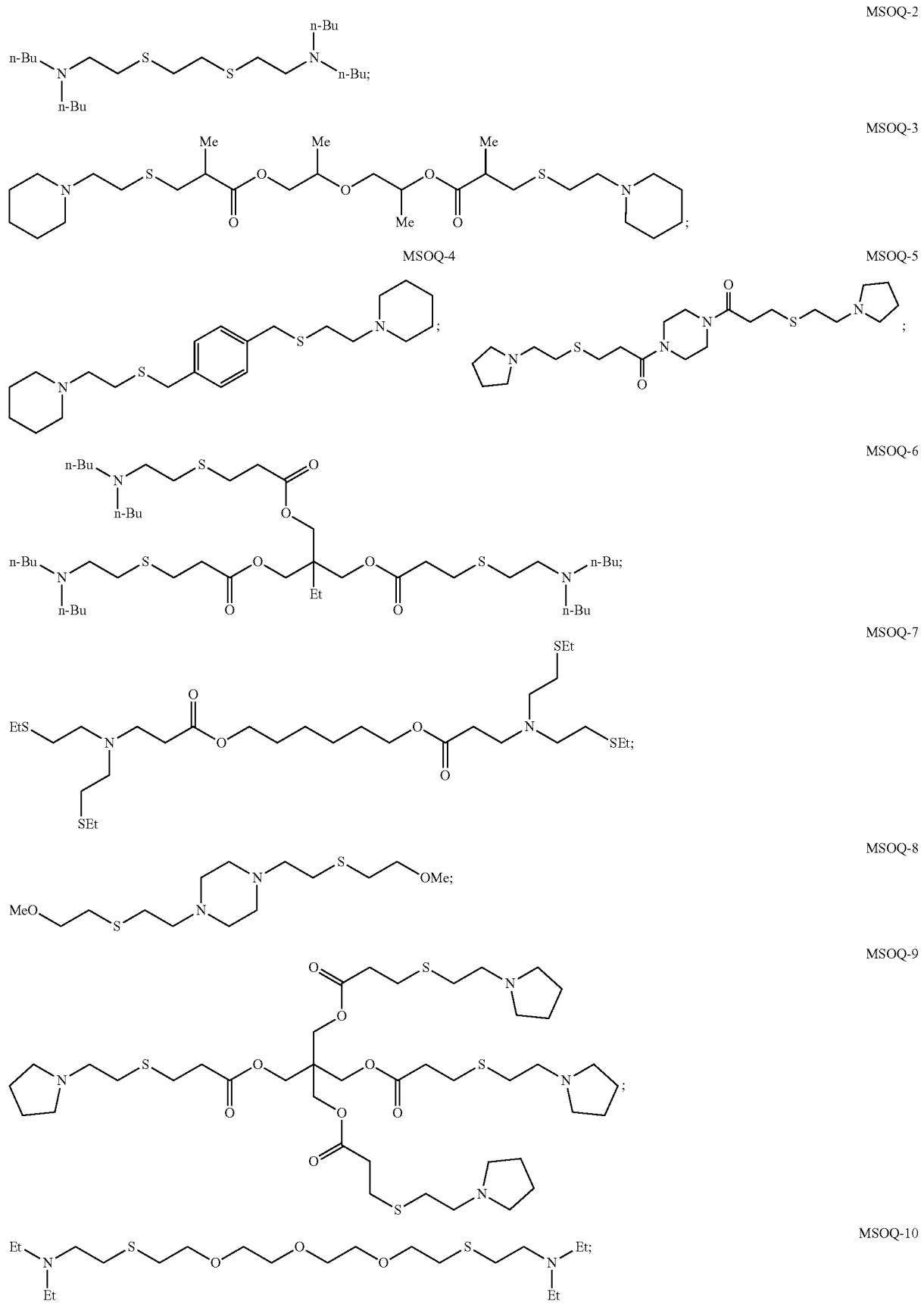

-continued
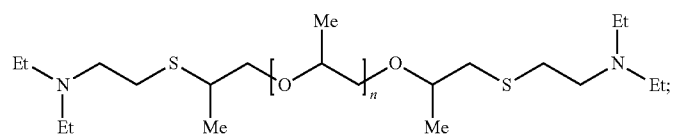
MSOQ-11
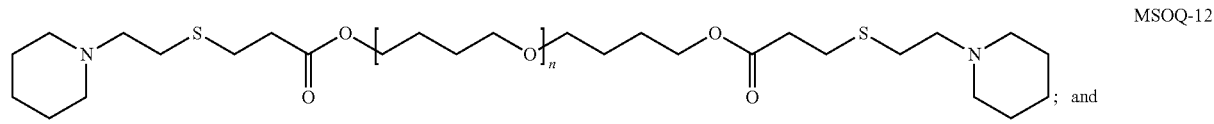
MSOQ-12
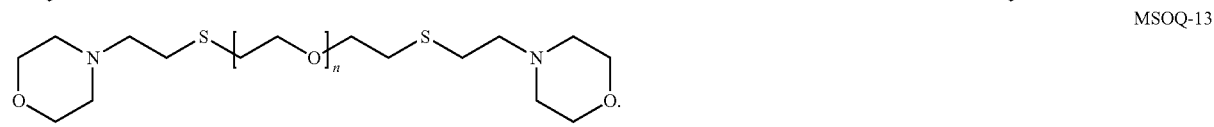
MSOQ-13
n = 9 on average
Particularly preferred examples of oligomeric and polymeric singlet oxygen quenchers include the compounds OSOQ-1 and OSOQ-2:
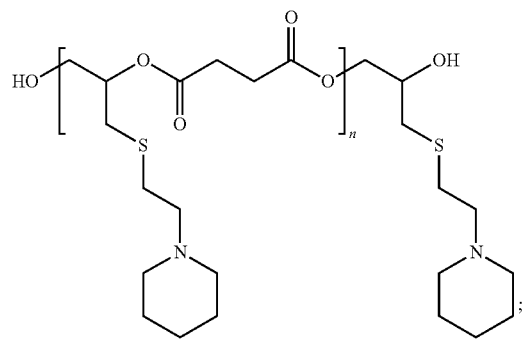
OSOQ-1
with n = 3 to 50
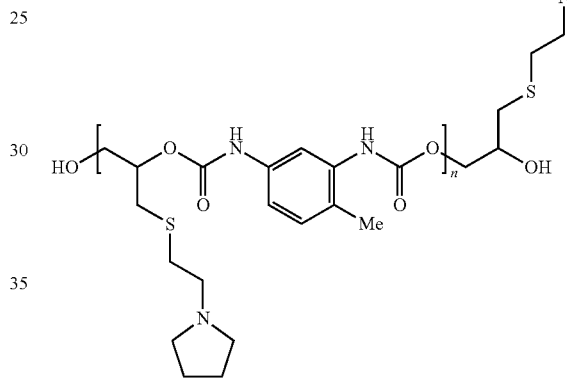
OSOQ-2
with n = 2 to 50
Particularly preferred examples of polymerizable singlet oxygen quenchers include the compounds PSOQ-1 to PSOQ-5:
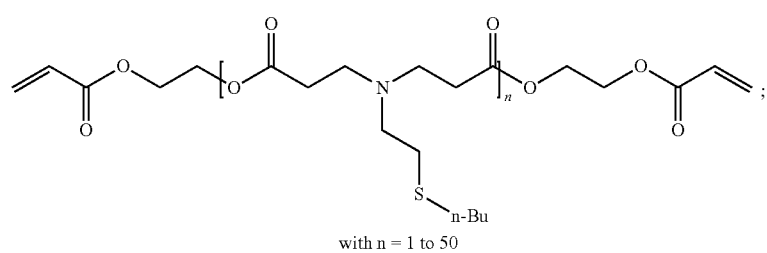
PSOQ-1
with n = 1 to 50
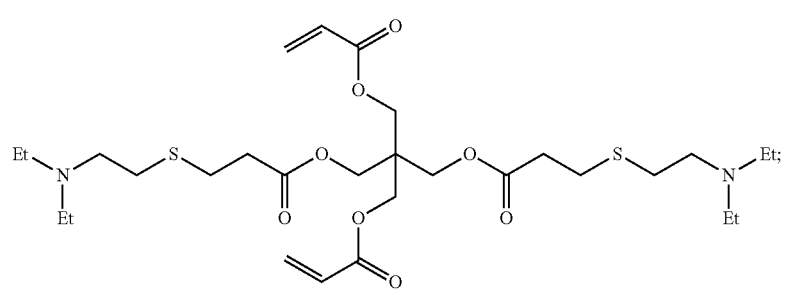
PSOQ-2

-continued

PSOQ-3

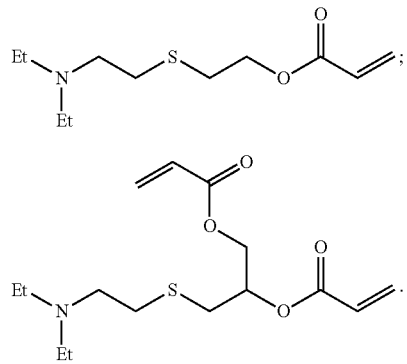

PSOQ-4

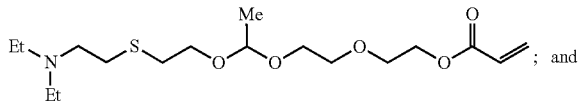; and

PSOQ-5

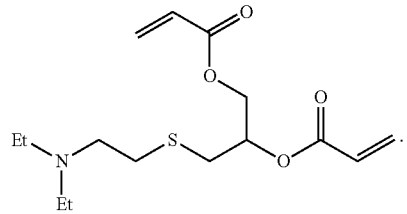

The ester group in the singlet oxygen quencher of the Formula (I) to (VI) is preferably a $C_1$-$C_6$-ester group, most preferably an ethylester group.

The amide group in the singlet oxygen quencher of the Formula (I) to (VI) is preferably a $C_1$-$C_6$-amide group, most preferably an ethylamide group.

The ketone group in the singlet oxygen quencher of the Formula (I) to (III) is preferably a $C_1$-$C_6$-ketone group, most preferably a methylketone or an ethylketone group.

The sulfone group in the singlet oxygen quencher according to general formula (I) to (V) is preferably introduced in said singlet oxygen quencher by addition of a thiol on a vinyl sulfone, where said vinyl sulfone is preferably further substituted by a group selected from an optionally substituted alkyl group and an optionally substituted aryl group, a $C_1$-$C_6$ alkyl group being more preferred.

The sulfonate ester group in the singlet oxygen quencher according to general formula (I) to (V) is preferably introduced in said singlet oxygen quencher by addition of a thiol on a vinyl sulfonate ester, where said vinyl sulfonate ester is an optionally substituted alkyl or aryl ester, a $C_1$-$C_6$ ester being more preferred, an ethyl ester being the most preferred.

The phosphonate group in the singlet oxygen quencher according to general formula (I) to (V) is preferably introduced in said singlet oxygen quencher by addition of a thiol on a vinyl phosphonate ester, where said vinyl phosphonate ester is an optionally substituted alkyl or aryl ester, a $C_1$-$C_6$ ester being more preferred, an ethyl ester being the most preferred.

In a particular preferred embodiment, the radiation curable inkjet ink of the invention includes at least one singlet oxygen quencher selected from the group consisting of the compounds SOQ-1 to SOQ-7 disclosed here above.

The singlet oxygen quenchers according to the invention may be used alone or in combination. It has been observed that a mixture of singlet oxygen quenchers have a super-additive effect in reducing the amount of aldehydes emitted after curing.

Synthesis of such compounds belongs to the normal skills of the skilled person in synthetical organic chemistry and is illustrated in the Examples hereinafter.

Polymerizable Compounds Including Vinylether or Vinylamide Groups

The polymerizable compound including a vinylether may be a monofunctional or polyfunctional polymerizable compound.

Preferred examples of monofunctional polymerizable compounds including a vinylether are ethyl vinyl ether, n-butyl vinyl ether, isobutyl vinyl ether, octadecyl vinyl ether, cyclohexyl vinyl ether, hydroxybutyl vinyl ether, 2-ethylhexyl vinyl ether, cyclohexanedimethanol monovinyl ether, n-propyl vinyl ether, isopropyl vinyl ether, isopropenyl vinyl ether, dodecyl vinyl ether, ethylene glycol monovinyl ether, diethylene glycol monovinyl ether, triethylene glycol monovinyl ether, octadecyl vinyl ether, hydroxyethyl monovinyl ether, and hydroxynonyl monovinyl ether.

Preferred examples of polyfunctional polymerizable compounds including a vinylether are ethylene glycol divinyl ether, diethylene glycol divinyl ether, triethylene glycol divinyl ether, propylene glycol divinyl ether, dipropylene glycol divinyl ether, butanediol divinyl ether, hexanediol divinyl ether, cyclohexane dimethanol divinyl ether, and trimethylolpropane trivinyl ether. Among these, triethylene glycol divinyl ether is particularly preferable because of good storage stability.

The polymerizable compound including a vinylether may also be a polyfunctional polymerizable compound having different types of polymerizable groups, preferably a vinylether group and a free radical polymerizable group selected from the group consisting of an acrylate, a methacrylate, an acrylamide and a methacrylamide. For the one or more free radical polymerizable groups, an acrylate and a methacrylate being more preferred, an acrylate being the most preferred.

A particularly preferred polymerizable compound including a vinylether is represented by Formula (VA-1):

$$CH2=CR1-COO-R2-O-CH=CH-R3 \qquad \text{Formula (VA-1)},$$

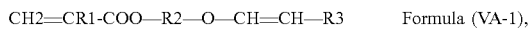

wherein R1 is a hydrogen atom or a methyl group, R2 is a divalent organic residue having 2 to 20 carbon atoms, and R3 is a hydrogen atom or a monovalent organic residue having 1 to 11 carbon atoms. Preferably, R2 divalent chain of 2 to 20 carbon atoms optionally interrupted by one or more oxygen atoms. Preferably R2 is a divalent chain of 2 to 20 carbon atoms optionally interrupted by one or more oxygen atoms.

In a preferred embodiment of the compound according to Formula (VA-1), R1 and R3 represent hydrogen.

In a more preferred embodiment of the compound according to Formula (VA-1), R1 and R3 represent hydrogen and R2 divalent chain of 2 to 20 carbon atoms optionally interrupted by one or more oxygen atoms.

Suitable examples of the compound of Formula (VA-1) include, but are not limited to, 2-vinyloxyethyl (meth)acrylate, 3-vinyloxypropyl (meth)acrylate, 1-methyl-2-vinyloxyethyl (meth)acrylate, 2-vinyloxypropyl (meth)acrylate, 4-vinyloxybutyl (meth)acrylate, 1-methyl-3-vinyloxypropyl (meth)acrylate, 1-vinyloxymethylpropyl (meth)acrylate, 2-methyl-3-vinyloxypropyl (meth)acrylate, 1,1-dimethyl-2-vinyloxyethyl (meth)acrylate, 3-vinyloxybutyl (meth)acrylate, 1-methyl-2-vinyloxypropyl (meth)acrylate, 2-vinyloxybutyl (meth)acrylate, 4-vinyloxycyclohexyl (meth)acrylate, 6-vinyloxyhexyl (meth)acrylate, 4-vinyloxymethylcyclohexylmethyl (meth)acrylate, 3-vinyloxymethylcyclohexylmethyl (meth)acrylate, 2-vinyloxymethylcyclohexylmethyl (meth)acrylate, vinyloxymethylphenylmethyl (meth)acrylate, m-vinyloxymethylphenylmethyl (meth)acrylate, o-vinyloxymethylphenylmethyl (meth)acrylate, 2-(2-vinyloxyethoxy)ethyl methacrylate, 2-(2-vinyloxyethoxy)ethyl acrylate (VEEA), 2-(vinyloxyisopropoxy) ethyl (meth)acrylate, 2-(vinyloxyethoxy)propyl (meth)acrylate, 2-(vinyloxyethoxy)isopropyl (meth)acrylate, 2-(vinyloxyisopropoxy)propyl (meth)acrylate, 2-(vinyloxyisopropoxy)isopropyl (meth)acrylate, 2-(vinyloxyethoxyethoxy)ethyl (meth)acrylate, 2-(vinyloxyethoxyisopropoxy) ethyl (meth)acrylate, 2-(vinyloxyisopropoxyethoxy)ethyl (meth)acrylate, 2-(vinyloxyisopropoxyisopropoxy)ethyl (meth)acrylate, 2-(vinyloxyethoxyethoxy)propyl (meth)acrylate, 2-(vinyloxyethoxyisopropoxy) propyl (meth)acrylate, 2-(vinyloxyisopropoxyethoxy) propyl (meth)acrylate, 2-(vinyloxyisopropoxyisopropoxy)propyl (meth)acrylate, 2-(vinyloxyethoxyethoxy) isopropyl (meth)acrylate, 2-(vinyloxyethoxyisopropoxy)isopropyl (meth)acrylate, 2-(vinyloxyisopropoxyethoxy)isopropyl (meth)acrylate, 2-(vinyloxyisopropoxyisopropoxy)isopropyl (meth)acrylate, 2-(vinyloxyethoxyethoxyethoxy)ethyl (meth)acrylate, 2-(vinyloxyethoxyethoxyethoxy)ethyl (meth)acrylate, 2-(isopropenoxyethoxy)ethyl (meth)acrylate, 2-(isopropenoxyethoxyethoxy)ethyl (meth)acrylate, 2-(isopropenoxyethoxyethoxy)ethyl (meth)acrylate, 2-(isopropenoxyethoxyethoxyethoxy)ethyl (meth)acrylate, polyethylene glycol monovinyl ether(meth)acrylate, and polypropylene glycol monovinyl ether(meth)acrylate.

2-(2-vinyloxyethoxy)ethyl acrylate is particularly preferred among the above examples, as it is advantageous in providing a good balance between the curability and the viscosity of the radiation curable inkjet ink.

The polymerizable compound including a vinylamide group is preferably a cyclic compound represented by Formula (NV-1):

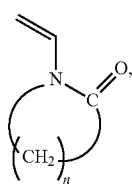

Formula (NV-1)

wherein n represents an integer of 2 to 6, n is preferably 3 or 5, and n is particularly preferably 5. Such compounds are also referred to as N-vinyllactams. The N-vinyllactam may have a substituent such as an alkyl group or an aryl group on the lactam ring, and may have a saturated or unsaturated ring structure bonded to the lactam ring.

Particularly preferred polymerizable compounds including a vinylamide are N-vinylcaprolactam and N-vinyl-2-pyrrolidone. Most preferably the polymerizable compounds including a vinylamide is N-vinylcaprolactam as it gives particularly good ink curability and adhesion of a cured ink layer to a recording medium, especially when N-vinylcaprolactam is present in the radiation curable inkjet ink in an amount of 8.0 wt %, preferably at least 10.0 wt % and most preferably at least 15 wt % based on the total weight of the radiation curable inkjet ink.

The polymerizable compound including a vinylether or a vinylamide may be used singly or in a combination of one or more polymerizable compounds including a vinylether or a vinylamide.

Other Polymerizable Compounds

The radiation curable inkjet ink of the invention may include other polymerizable compounds than the polymerizable compound including a vinylether group or a vinylamide group. Any monomer and oligomer capable of free radical polymerization may be used in the radiation curable inkjet inks. The monomers and oligomers may have different degrees of polymerizable functionality, and a mixture including combinations of mono-, di-, tri- and higher polymerizable functionality monomers may be used. The viscosity of the radiation curable inkjet ink can be adjusted by varying the ratio between the monomers.

For minimizing bad smell and health risks, the monomers and oligomers used are preferably purified compounds having no or almost no impurities, more particularly no toxic or carcinogenic impurities. The impurities are usually derivative compounds obtained during synthesis of the polymerizable compound. Purification methods are well-known to those skilled in the art of manufacturing monomers and oligomers. Sometimes, however, some compounds may be added deliberately to pure polymerizable compounds in harmless amounts, for example, polymerization inhibitors or stabilizers.

Particularly preferred monomers and oligomers are those listed in [0106] to [0113] of EP 1911814 A (AGFA).

Photoinitiators

The radiation curable inkjet ink preferably also contains a photoinitiator. A photoinitiator requires less energy to activate than the polymerizable compounds for forming a polymer. If the free radical inkjet ink contains no initiator, it can be cured by electron beam curing.

The radiation curable inkjet ink more preferably contains a photoinitiating system comprising one or more photoinitiators and one or more co-initiators instead of a single photoinitiator.

The photoinitiator in the curable inkjet ink may be a Norrish type I initiator or a Norrish type II initiator. Such a photoinitiator is a chemical compound that initiates polymerization of monomers and oligomers when exposed to actinic radiation by the formation of a free radical. A Norrish Type I initiator is an initiator which cleaves after excitation, yielding the initiating radical immediately. A Norrish type II-initiator is a photoinitiator which is activated by actinic radiation and forms free radicals by hydrogen abstraction from a second compound that becomes the actual initiating free radical. This second compound is called a polymerization synergist or a co-initiator. Both type I and type II photoinitiators can be used in the present invention, alone or in combination.

Norrish Type II Photoinitiators

The radiation curable inkjet ink preferably contains a Norrish Type II photoinitiator including a photoinitiating moiety selected from the group consisting of a thioxanthone group and a benzophenone group. A Norrish Type II photoinitiator containing a thioxanthone group is particularly preferred as it is advantageous for UV LED curing, especially for UV LEDs having an emission wavelength of 360 nm or even 370 nm.

Suitable examples of Norrish Type II photoinitiators containing a thioxanthone group include, but are not particularly limited to, thioxanthone; diethylthioxanthone, such as 2,4-diethylthioxanthone; isopropylthioxanthone, such as 2-isopropylthioxanthone and 4-isopropylthioxanthone; and chlorothioxanthone, such as 2-chlorothioxanthone.

Specific examples of commercially available Norrish Type II photoinitiators containing a thioxanthone group are Speedcure™ DETX (2,4-diethylthioxanthone) and Speedcure™ ITX (2-isopropylthioxanthone) from LAMBSON and Kayacure™ DETX-S (2,4-diethylthioxanthone) from Nippon Kayaku Co.

Suitable examples of Norrish Type II photoinitiators containing a benzophenone group include, but are not particularly limited to, benzophenone; methylbenzophenone; methyl-2-benzoylbenzoate, phenylbenzophenone, such as 4-phenylbenzophenone; trimethylbenzophenone; bis(alkylamino)benzophenone; and 4-(dialkylamino)benzophenone.

Specific examples of commercially available Norrish Type II photoinitiators containing a benzophenone group are Omnirad™ 4 MBZ and Omnirad™ BP from IGM RESINS, Speedcure™ PBZ and Speedcure™ 5040 from LAMBSON. The latter is a mixture of benzophenone and thioxanthone.

The content of the Norrish Type II photoinitiator including a photoinitiating moiety selected from the group consisting of a thioxanthone group and a benzophenone group is preferably 0.5 to 7.5 wt %, more preferably 1 to 5 wt % based on the total weight of the radiation curable inkjet ink. However, if the Norrish Type II photoinitiator is a polymerizable or a polymeric thioxanthone compound, the content may be higher, preferably up to 25 wt %, more preferably up to 15 wt % based on the total weight of the radiation curable inkjet ink.

Preferred examples of polymerizable Norrish Type II photoinitiators including a photoinitiating moiety selected from the group consisting of a thioxanthone group or a benzophenone group are disclosed in EP 2161264 A (AGFA), EP 2199273 A (AGFA) and EP 2684876 A (AGFA).

Preferred examples of polymeric Norrish Type II photoinitiators including a photoinitiating moiety selected from the group consisting of a thioxanthone group or a benzophenone group are disclosed in EP 1616920 A (AGFA) and EP 1616899 A (AGFA).

Commercial examples of polymeric thioxanthones and benzophenones include Omnipol™ BP, Omnipol™ TX, and Omnipol™ 2702 from IGM RESINS.

Acylphosphine Oxide and α-Hydroxy Ketone Photoinitiators

Aldehydes can also be formed as photodecomposition by-products upon UV exposure from acylphosphine oxide photoinitiators and α-hydroxy ketone photoinitiators. Scheme 1 here below shows how a trimethylbenzoyl radical is formed upon UV exposure, which after abstracting hydrogen from a suitable H-donor present in the radiation curable inkjet ink leads to trimethylbenzaldehyde (mesitaldehyde) having a characteristic almond odour. The phosphine oxide radical initiates the polymerization reaction of the polymerizable compounds present in the radiation curable inkjet ink.

Scheme 1 formation of aldehyde from 2,4,6-trimethyl diphenyl phosphine oxide

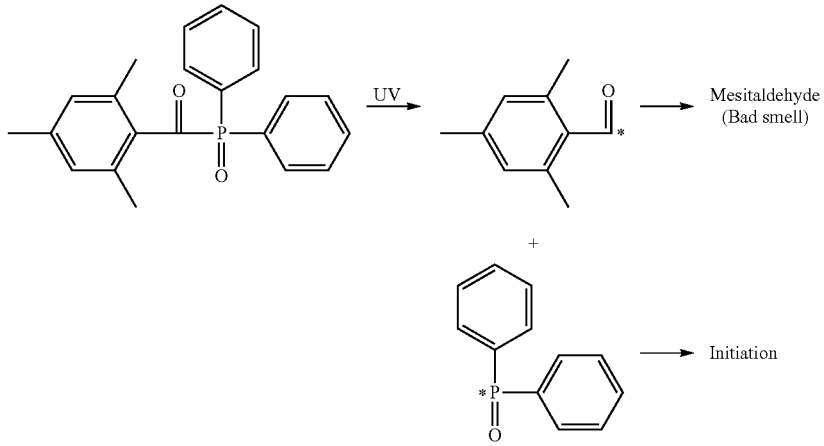

As an example for the aldehyde formation from a α-hydroxy ketone photoinitiator, the scheme 2 is given where benzaldehyde is formed from the benzoyl radical after hydrogen abstraction.

Scheme 2 formation of aldehyde from 1-hydroxycyclohexyl phenyl ketone

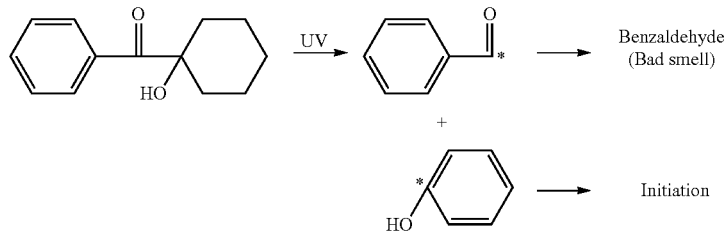

An acylphosphine oxide photoinitiator is particularly advantageous for curability when UV curing is performed with UV LEDs having a long wavelength of more than 360 nm, especially when the acylphosphine oxide photoinitiator is further combined with a Norrish Type II photoinitiator containing a thioxanthone group.

Preferred examples of the acylphosphine oxide photoinitiators include, but are not particularly limited to, a bis(2,4,6-trimethylbenzoyl)-phenyl phosphine oxide, a 2,4,6-trimethylbenzoyl-diphenyl-phosphine oxide, and a bis-(2,6-dimethoxybenzoyl)-2,4,4-trimethylpentyl phosphine oxide Preferred commercially available acylphosphine oxide photoinitiators include, but are not particularly limited to, Irgacure™ 819 (bis(2,4,6-trimethyl benzoyl)-phenyl phosphine oxide) and Darocur™ TPO (2,4,6-trimethyl benzoyl-diphenyl-phosphine oxide) both available from BASF, and Speedcure™ TPO-L (Ethyl(2,4,6-trimethylbenzoyl)phenyl phosphinate) from LAMBSON.

The content of the acylphosphine oxide photoinitiator is preferably 3 to 15 wt %, more preferably 5 to 13 wt %, and still more preferably 6 to 10 wt % based on the total weight of the radiation curable inkjet ink.

Examples of the α-hydroxy ketone photoinitiators include, but are not particularly limited to, 1-hydroxycyclohexyl phenyl ketone, 2-hydroxy-2-methyl-1-phenyl propane-1-one and 1-[4-(2-hydroxyethoxy)-phenyl]2-hydroxy-2-methyl-1-propane-1-on.

Examples of commercially α-hydroxy ketone photoinitiators include, but are not particularly limited to, Darocur™ 1173, Irgacure™ 184 and Irgacure™ 127 from BASF, Speedcure™ 2022 from LAMBSON and Omnirad™ 4817 from IGM RESINS.

The content of the α-hydroxy ketone is preferably 1 to 10 wt %, more preferably 2 to 8 wt %, and still more preferably 3 to 6 wt % based on the total weight of the radiation curable inkjet ink.

In a preferred embodiment, the one or more acyl groups of the acylphosphine oxide photoinitiator or α-hydroxy ketone photoinitiator are connected to a polymer or to a polymerizable group. The acyl group of the photoinitiators of Scheme 1 and 2 form benzoyl radicals, which after hydrogen abstraction form aldehydes resulting in a distinct smell of cured ink layers. When these aldehydes are connected to a polymer or to a polymerizable group, they become diffusion hindered and the smell is minimized as they remain almost fully in the cured ink layer.

Suitable polymeric acylphosphine oxide photoinitiators are disclosed in EP 2960303 A (FUJIFILM).

A preferred example of a polymerizable acylphosphine oxide photoinitiator is the compound UREA-2 given here below in our Example 3.

An example of a suitable polymeric α-hydroxy ketone photoinitiator is available as Esacure™ KIP150 from IGM RESINS.

Suitable polymerizable α-hydroxy ketone photoinitiators are disclosed in U.S. Pat. No. 4,922,004 (MERCK), such as 4-(2-acryloyloxyethoxy)-phenyl 2-acryloyloxy-2-propyl ketone prepared in Example 3.

Other Photoinitiators

Instead or in addition of the Norrish Type II photoinitiators including a photoinitiating moiety selected from the group consisting of a thioxanthone group or a benzophenone group, the acylphosphine oxide photoinitiators and the α-hydroxy ketone photoinitiators, the radiation curable inkjet ink may contain other free radical photoinitiators. Other suitable photoinitiators may, for example, be selected from those are disclosed in CRIVELLO, J. V., et al. Photoinitiators for Free Radical Cationic and Anionic Photopolymerization. 2nd edition. Edited by BRADLEY, G. London, UK: John Wiley and Sons Ltd, 1998. p. 287-294.

Preferred other photoinitiators are selected from the group consisting of benzoinethers, benzil ketals, α,α-dialkoxyacetophenones, α-aminoalkylphenones, acylphosphine sulphides, α-haloketones, α-halosulfones, α-halophenylglyoxalates,1,2-diketones and anthraquinones.

Co-Initiators

In order to increase the photosensitivity further, the radiation curable ink may additionally contain co-initiators, also called polymerization synergists, for which usually amine synergists are used.

Suitable examples of amine synergists can be categorized in three groups:
1) tertiary aliphatic amines such as methyldiethanolamine, dimethylethanolamine, triethanolamine, triethylamine and N-methylmorpholine;
(2) aromatic amines such as amylparadimethylaminobenzoate, 2-n-butoxyethyl-4-(dimethylamino)benzoate, 2-(dimethylamino)ethylbenzoate, ethyl-4-(dimethylamino)benzoate, and 2-ethylhexyl-4-(dimethylamino) benzoate; and
(3) (meth)acrylated amines such as dialkylamino alkyl (meth)acrylates (e.g., diethylaminoethylacrylate) or N-morpholinoalkyl-(meth)acrylates (e.g., N-morpholinoethyl-acrylate).

A preferred group of effective amine synergists are alkanolamines. However, these compounds are also very susceptible to hydrolysis leading to the formation of aldehydes, such as formaldehyde. An example of such a hydrolysis scheme is given here below in Scheme 3.

Scheme 3 formation of aldehyde from an alkanolamine

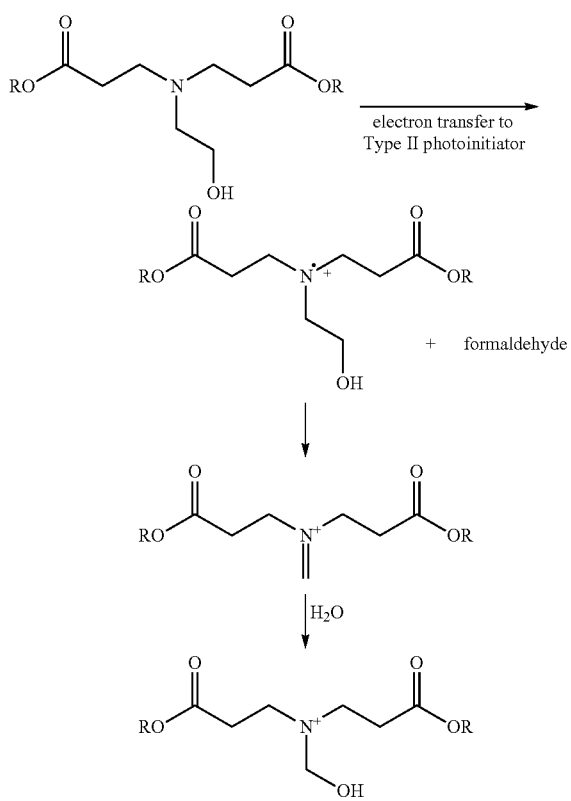

It was found that radiation curable inkjet inks could contain large amount of alkanolamines, such as e.g. Sartomer™ CN3755 from ARKEMA, while formaldehyde production was effectively minimized if singlet oxygen quenchers according to invention were present.

In another aspect of the invention, a preferred embodiment of a radiation curable inkjet ink includes a) at least 3 wt % of a compound including an alkanolamine group based on the total weight of the radiation curable inkjet ink; and
b) a singlet oxygen quencher including at least one amino-thioether group according to Formula (I):

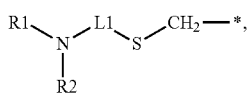

Formula (I)

wherein
* represents the point of attachment in the singlet oxygen quencher;
L1 represents a divalent linking group positioning X and N in a 1 to 2 to a 1 to 4 position;
R1 and R2 are independently selected from the group consisting of a $C_1$-$C_6$-alkyl group, a $C_2$-$C_6$-alkyl group which is interrupted by one oxygen atom and/or an ester group, a $C_2$-$C_6$-alkenyl group, a $C_2$-$C_6$-alkenyl group which is interrupted by one oxygen atom and/or an ester group, a $C_2$-$C_6$-alkynyl group, a $C_2$-$C_6$-alkynyl group which is interrupted by one oxygen atom and/or an ester group, a $C_7$-$C_{12}$-aralkyl group; or any of R1, R2, S and L1 may represent the necessary atoms to form a five to eight membered ring. The amine synergist including an alkanolamine group is preferably a compound wherein the nitrogen and hydroxylgroup are spaced apart by 1 to 4 carbon atoms.

An alkanol amine co-initiator is preferably defined as an amine synergist according to Formula (A-1):

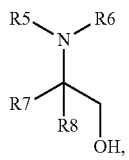

Formula (A-1)

wherein $R_5$ and $R_6$ are independently selected from the group consisting of a substituted or unsubstituted alkyl group, a substituted or unsubstituted alkenyl group, a substituted or unsubstituted alkynyl group and a substituted or unsubstituted aralkyl group; $R_7$ and R8 are independently selected from the group consisting of a hydrogen, a substituted or unsubstituted alkyl group, a substituted or unsubstituted alkenyl group, a substituted or unsubstituted alkynyl group and a substituted or unsubstituted aralkyl group; and wherein any of R5 to $R_8$ may represent the necessary atoms to form a five to eight membered ring. In a particularly preferred embodiment R7 and R8 represent a hydrogen.

In a further preferred embodiment, the amine synergist is a compound according to Formula (A-2):

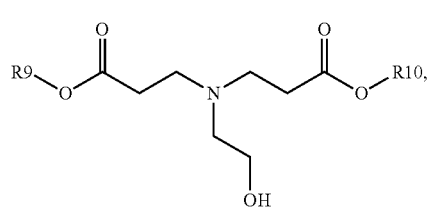

Formula (A-2)

wherein $R_9$ and $R_{10}$ are independently selected from the group consisting of a substituted or unsubstituted alkyl group, a substituted or unsubstituted alkenyl group, a substituted or unsubstituted alkynyl group and a substituted or unsubstituted aralkyl group.

Preferred amine synergists including an alkanolamine group include triethanolamine (TEA) and methyl di-ethanolamine (MDEA).

Preferred examples of amine synergists including an alkanolamine group are given in Table 1 without being limited thereto

TABLE 1

| | |
|---|---|
| 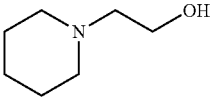 | Alkanol-1 |
| 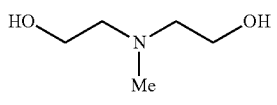 | Alkanol-2 |
| 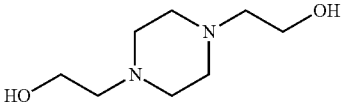 [SMILES: OCCN1CCN(CCO)CC1] | Alkanol-3 |
| 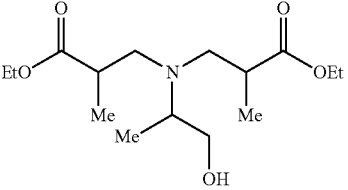 | Alkanol-4 |

TABLE 1-continued

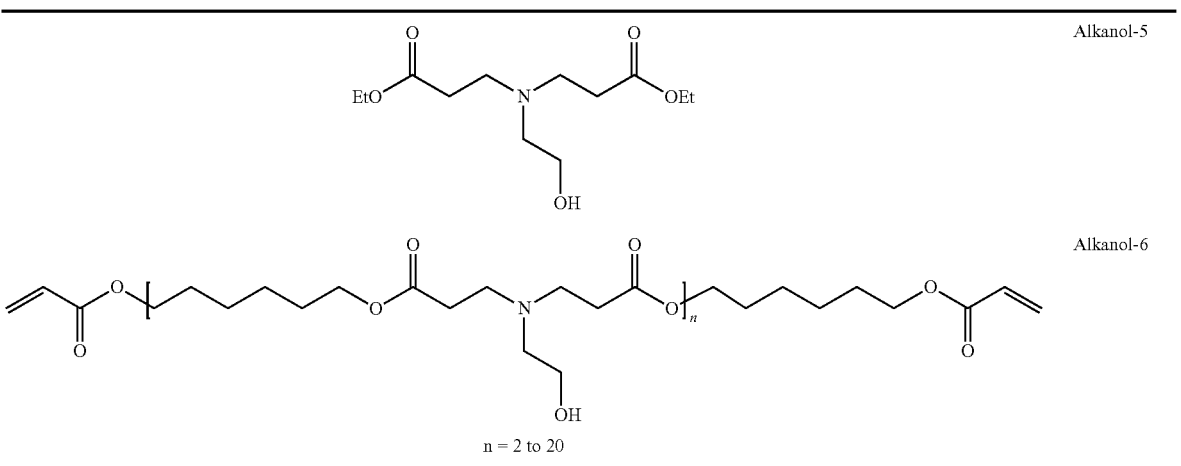

Alkanol-5

Alkanol-6 n = 2 to 20

In the most preferred embodiment, the amine synergist including an alkanolamine group is a polymeric or oligomeric co-initiator obtained by the condensation of 2-hydroxy-ethylamine and a difunctional acrylate or methacrylate, a difunctional acrylate being particularly preferred. A particularly preferred commercially available amine synergist including an alkanolamine group is Sartomer™ CN3755 containing the compound AA-1:

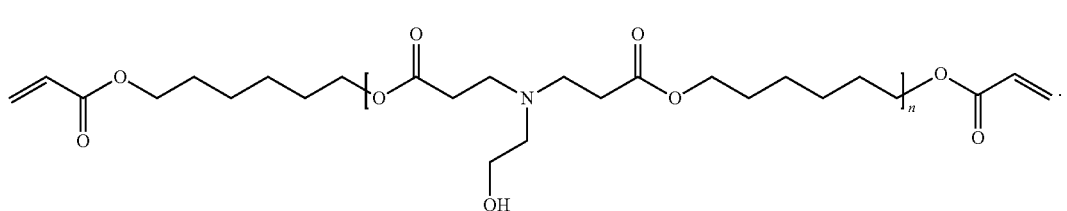

compound AA-1

In a preferred embodiment, the amine synergist including an alkanolamine group or a dimethyl benzoate group is present in an amount of 4 to 20 wt %, more preferably 5 to 15 wt % and most preferably 6 to 10 wt % based on the total weight of the radiation curable inkjet ink. In such ranges, excellent curability is obtained.

For certain inkjet applications, the one or more co-initiators are diffusion hindered for safety reasons. A diffusion hindered co-initiator is preferably selected from the group consisting of non-polymeric di- or multifunctional co-initiators, oligomeric or polymeric co-initiators and polymerizable co-initiators. More preferably the diffusion hindered co-initiator is selected from the group consisting of polymeric co-initiators and polymerizable co-initiators. For the lowest impact on viscosity, most preferably the diffusion hindered co-initiator is a polymerizable co-initiator having at least one (meth)acrylate group, more preferably having at least one acrylate group. A preferred compound including an alkanolamine group is the acrylated amine polymerization synergist Sartomer™ CN3755 from ARKEMA.

The radiation curable inkjet ink preferably includes a polymerizable or polymeric tertiary amine co-initiator.

Preferred diffusion hindered co-initiators are the polymerizable co-initiators disclosed in EP 2053101 A (AGFA) in paragraphs [0088] and [0097].

Preferred diffusion hindered co-initiators include a polymeric co-initiator having a dendritic polymeric architecture, more preferably a hyperbranched polymeric architecture. Preferred hyperbranched polymeric co-initiators are those disclosed in US 2006014848 A (AGFA).

The radiation curable inkjet ink preferably includes the (diffusion hindered) co-initiator in an amount of 0.1 to 50 wt %, more preferably in an amount of 0.5 to 25 wt %, most preferably in an amount of 1 to 15 wt % of the total weight of the inkjet ink.

Colorants

The radiation curable inkjet ink may contain a colorant. Colorants used in the inkjet inks may be dyes, pigments or a combination thereof. Organic and/or inorganic pigments are preferred because of their migration-fastness and their superior light fading properties compared to dyes.

The pigments may be black, white, cyan, magenta, yellow, red, orange, violet, blue, green, brown, mixtures thereof, and the like. This colour pigment may be chosen from those disclosed by HERBST, Willy, et al. Industrial Organic Pigments, Production, Properties, Applications. 3rd edition. Wiley—VCH, 2004. ISBN 3527305769.

Particular preferred pigments are C.I. Pigment Yellow 1, 3, 10, 12, 13, 14, 17, 55, 65, 73, 74, 75, 83, 93, 97, 109, 111, 120, 128, 138, 139, 150, 151, 154, 155, 175, 180, 181, 185, 194 and 213.

Particular preferred pigments are C.I. Pigment Red 17, 22, 23, 41, 48:1, 48:2, 49:1, 49:2, 52:1, 57:1, 88, 112, 122, 144, 146, 149, 170, 175, 176, 184, 185, 188, 202, 206, 207, 210, 216, 221, 248, 251, 254, 255, 264, 266, 270 and 272.

Particular preferred pigments are C.I. Pigment Violet 19, 23, 32, and 37.

Particular preferred pigments are C.I. Pigment Blue 15:1, 15:2, 15:3, 15:4, 15:6, 16, 56, 61 and (bridged) aluminium phthalocyanine pigments.

Particular preferred pigments are C.I. Pigment Orange 5, 13, 16, 34, 40, 43, 59, 66, 67, 69, 71 and 73.

Particular preferred pigments are C.I. Pigment Green 7 and 36.

Particular preferred pigments are C.I. Pigment Brown 6 and 7.

Suitable pigments include mixed crystals of the above particular preferred pigments. Mixed crystals are also referred to as solid solutions. For example, under certain conditions different quinacridones mix with each other to form solid solutions, which are quite different from both physical mixtures of the compounds and from the compounds themselves. In a solid solution, the molecules of the components enter into the same crystal lattice, usually, but not always, that of one of the components. The x-ray diffraction pattern of the resulting crystalline solid is characteristic of that solid and can be clearly differentiated from the pattern of a physical mixture of the same components in the same proportion. In such physical mixtures, the x-ray pattern of each of the components can be distinguished, and the disappearance of many of these lines is one of the criteria of the formation of solid solutions. A commercially available example is Cinquasia™ Magenta RT-355-D from BASF AG.

Carbon black is preferred as a black pigment. Suitable black pigments include carbon blacks such as Pigment Black 7 (e.g. Carbon Black MA8® from MITSUBISHI CHEMICAL), Regal® 400R, Mogul® L, Elftex® 320 from CABOT Co., or Carbon Black FW18, Special Black 250, Special Black 350, Special Black 550, Printex® 25, Printex® 35, Printex® 55, Printex® 90, Printex® 150T from DEGUSSA. In a preferred embodiment, the carbon black pigment used is a pigment having less than 0.15% of toluene-extractable fraction using the method as described in section III, paragraph 5 of the Resolution AP(89) 1 dated 13 Sep. 1989 published by the Council of Europe.

It is also possible to make mixtures of pigments. For example, in some inkjet ink application a neutral black inkjet ink is preferred and can be obtained e.g. by mixing a black pigment and a cyan pigment into the ink. Also pigments may be combined to enlarge the colour gamut of an ink set. The inkjet ink set may also include one or more spot colours. Silver and gold are often desired colours for making a product more attractive by giving it an exclusive appearance.

Also non-organic pigments may be present in the inks. Suitable pigments are C.I. Pigment Metal 1, 2 and 3. Illustrative examples of the inorganic pigments include titanium oxide, barium sulfate, calcium carbonate, zinc oxide, lead sulfate, yellow lead, zinc yellow, red iron oxide (III), cadmium red, ultramarine blue, prussian blue, chromium oxide green, cobalt green, amber, titanium black and synthetic iron black. However, care should be taken to prevent migration and extraction of heavy metals in food application. Preferably no pigments are used which contain a heavy metal selected from the group consisting of arsenic, lead, mercury and cadmium. In a more preferred embodiment, no inorganic pigments are used in the inkjet ink with the exception of titanium oxide or calcium carbonate for the optional white inkjet ink.

Pigment particles in inkjet ink should be sufficiently small to permit free flow of the ink through the inkjet-printing device, especially at the ejecting nozzles. It is also desirable to use small particles for maximum colour strength and to slow down sedimentation.

The numeric average pigment particle size is preferably between 0.050 and 1 μm, more preferably between 0.070 and 0.300 μm and particularly preferably between 0.080 and 0.200 μm. Most preferably, the numeric average pigment particle size is no larger than 0.150 μm. An average particle size smaller than 0.050 μm is less desirable for decreased light-fastness, but mainly also because very small pigment particles or individual pigment molecules thereof may still be extracted in food packaging applications.

The numeric average pigment particle size of pigment particles is best determined with a Brookhaven Instruments Particle Sizer BI90 plus based upon the principle of dynamic light scattering. The ink is then diluted, for example, with ethyl acetate to a pigment concentration of 0.002 wt %. The measurement settings of the BI90 plus are: 5 runs at 23° C., angle of 90°, wavelength of 635 nm and graphics=correction function.

In the case of a white inkjet ink, preferably a pigment with a refractive index greater than 1.60, preferably greater than 2.00, more preferably greater than 2.50 and most preferably greater than 2.60 is used. The white pigments may be employed singly or in combination.

Preferably titanium dioxide is used for the pigment with a refractive index greater than 1.60. Titanium oxide occurs in the crystalline forms of anatase type, rutile type and brookite type. The anatase type has a relatively low density and is easily ground into fine particles, while the rutile type has a relatively high refractive index, exhibiting a high covering power. Either one of these is usable in this invention. It is preferred to make the most possible use of characteristics and to make selections according to the use thereof. The use of the anatase type having a low density and a small particle size can achieve superior dispersion stability, ink storage stability and ejectability. At least two different crystalline forms may be used in combination. The combined use of the anatase type and the rutile type which exhibits a high colouring power can reduce the total amount of titanium oxide, leading to improved storage stability and ejection performance of ink.

For surface treatment of the titanium oxide, an aqueous treatment or a gas phase treatment is applied, and an alumina-silica treating agent is usually employed. Untreated-, alumina treated- or alumina-silica treated-titanium oxide are employable.

The numeric average particle diameter of the titanium oxide or other white pigments is preferably from 50 to 500 nm, more preferably from 150 to 400 nm, and most preferably from 200 to 350 nm. Sufficient hiding power cannot be obtained when the average diameter is less than 50 nm, and the storage ability and the jet-out suitability of the ink tend to be degraded when the average diameter exceeds 500 nm. The determination of the numeric average particle diameter is best performed by photon correlation spectroscopy at a wavelength of 633 nm with a 4 mW HeNe laser on a diluted sample of the pigmented inkjet ink. A suitable particle size analyzer used was a Malvern™ nano-S available from Goffin-Meyvis. A sample can, for example, be prepared by addition of one drop of ink to a cuvette containing 1.5 mL ethyl acetate and mixed until a homogenous sample was obtained. The measured particle size is the average value of 3 consecutive measurements consisting of 6 runs of 20 seconds.

Generally, pigments are stabilized in the dispersion medium by dispersing agents, such as polymeric dispersants or surfactants. However, the surface of the pigments can be modified to obtain so-called "self-dispersible" or "self-dispersing" pigments, i.e. pigments that are dispersible in the dispersion medium without dispersants.

The pigment is preferably used in a pigment dispersion used for preparing inkjet inks in an amount of 10 to 40 wt %, more preferably of 15 to 30 wt % based on the total weight of the pigment dispersion. In a coloured inkjet ink the pigment is preferably present in an amount of 0.1 to 20 wt %, preferably 1 to 13 wt % based on the total weight of the inkjet ink.

Dispersants

The radiation curable inkjet ink may also contain a dispersant in order to further improve pigment dispersion properties. Examples of the dispersant include, but are not particularly limited to, dispersants commonly used for preparing a pigment dispersion liquid, such as a polymer dispersant, for example.

Typical polymeric dispersants are copolymers of two monomers but may contain three, four, five or even more monomers. The properties of polymeric dispersants depend on both the nature of the monomers and their distribution in the polymer. Copolymeric dispersants preferably have the following polymer compositions:

- statistically polymerized monomers (e.g. monomers A and B polymerized into ABBAABAB);
- alternating polymerized monomers (e.g. monomers A and B polymerized into ABABABAB);
- gradient (tapered) polymerized monomers (e.g. monomers A and B polymerized into AAABAABBABBB);
- block copolymers (e.g. monomers A and B polymerized into AAAAABBBBBB) wherein the block length of each of the blocks (2, 3, 4, 5 or even more) is important for the dispersion capability of the polymeric dispersant;
- graft copolymers (graft copolymers consist of a polymeric backbone with polymeric side chains attached to the backbone); and
- mixed forms of these polymers, e.g. blocky gradient copolymers.

Suitable polymeric dispersants are listed in the section on "Dispersants", more specifically [0064] to [0070] and [0074] to [0077], in EP 1911814 A (AGFA GRAPHICS) incorporated herein as a specific reference.

The polymeric dispersant has preferably a number average molecular weight Mn between 500 and 30000, more preferably between 1500 and 10000.

The polymeric dispersant has preferably a weight average molecular weight Mw smaller than 100,000, more preferably smaller than 50,000 and most preferably smaller than 30,000.

The polymeric dispersant has preferably a polydispersity PD smaller than 2, more preferably smaller than 1.75 and most preferably smaller than 1.5.

Commercial examples of polymeric dispersants are the following:

- DISPERBYK™ dispersants available from BYK CHEMIE GMBH;
- SOLSPERSE™ dispersants available from LUBRIZOL;
- TEGO™ DISPERS™ dispersants from EVONIK;
- EDAPLAN™ dispersants from MÜNZING CHEMIE;
- ETHACRYL™ dispersants from LYONDELL;
- GANEX™ dispersants from ISP;
- DISPEX™ and EFKA™ dispersants from BASF;
- DISPONER™ dispersants from DEUCHEM.

Particularly preferred polymeric dispersants include Solsperse™ dispersants from LUBRIZOL, Efka™ dispersants from BASF, Disperbyk™ dispersants from BYK CHEMIE GMBH, and Ajisper™ dispersants from AJINOMOTO FINE-TECHNO Co. Particularly preferred dispersants are Solsperse™ 32000, 35000 and 39000 dispersants from LUBRIZOL.

The dispersants may be used alone or in combination of two or more kinds thereof.

The polymeric dispersant is preferably used in an amount of 2 to 600 wt %, more preferably 5 to 200 wt %, most preferably 50 to 90 wt % based on the weight of the pigment.

Dispersion Synergists

A dispersion synergist usually consists of an anionic part and a cationic part. The anionic part of the dispersion synergist exhibiting a certain molecular similarity with the colour pigment and the cationic part of the dispersion synergist consists of one or more protons and/or cations to compensate the charge of the anionic part of the dispersion synergist.

The dispersion synergist is preferably added in a smaller amount than the polymeric dispersant(s). The ratio of polymeric dispersant/dispersion synergist depends upon the pigment and should be determined experimentally. Typically the ratio wt % polymeric dispersant/wt % dispersion synergist is selected between 2:1 to 100:1, preferably between 2:1 and 20:1.

Suitable dispersion synergists that are commercially available include Solsperse™ 5000 and Solsperse™ 22000 from LUBRIZOL.

Particular preferred pigments for the magenta ink used are a diketopyrrolo-pyrrole pigment or a quinacridone pigment. Suitable dispersion synergists include those disclosed in EP 1790698 A (AGFA GRAPHICS), EP 1790696 A (AGFA GRAPHICS), WO 2007/060255 (AGFA GRAPHICS) and EP 1790695 A (AGFA GRAPHICS).

In dispersing C.I. Pigment Blue 15:3, the use of a sulfonated Cu-phthalocyanine dispersion synergist, e.g. Solsperse™ 5000 from LUBRIZOL is preferred. Suitable dispersion synergists for yellow inkjet inks include those disclosed in EP 1790697 A (AGFA GRAPHICS).

Polymerization Inhibitors

The radiation curable inkjet ink may also contain a polymerization inhibitor. Due to the fact that an ink contains the polymerization inhibitor, a polymerization reaction before curing can be prevented.

Suitable polymerization inhibitors include phenol type antioxidants, hindered amine light stabilizers, phosphor type antioxidants, benzoquinone, hydroquinone and derivatives, such as hydroquinone monomethyl ether commonly used in (meth)acrylate monomers.

Examples of the phenolic polymerization inhibitor include, but are not limited to the following substances, p-methoxy phenol, cresol, t-butyl catechol, di-t-butyl-p-cresol, hydroquinone monomethylether, α-naphthol, 3,5-di-t-butyl-4-hydroxytoluene, 2,6-di-t-butyl-4-methylphenol, 2,2'-methylene-bis(4-methyl-6-t-butylphenol), 2,2'-methylene-bis(4-ethyl-6-butylphenol), and 4,4'-thio-bis(3-methyl-6-t-butylphenol) and pyrogallol.

Suitable commercial inhibitors are, for example, Sumilizer™ GA-80, Sumilizer™ GM and Sumilizer™ GS produced by Sumitomo Chemical Co. Ltd.; Genorad™ 16, Genorad™ 18 and Genorad™ 20 from Rahn AG; Irgastab™ UV10 and Irgastab™ UV22, Tinuvin™ 460 and CGS20 from Ciba Specialty Chemicals; Floorstab™ UV range (UV-1, UV-2, UV-5 and UV-8) from Kromachem Ltd, Additol™ S range (S100, S110, S120 and S130) from Cytec Surface Specialties.

A preferred polymerization inhibitor is Irgastab™ UV10 from BASF. Other examples of polymerization inhibitor include TEMPO, TEMPOL, and AI cupferron.

The polymerization inhibitors may be used alone or in combination of two or more kinds thereof.

In a preferred embodiment, the polymerization inhibitor is a mixture of different types of polymerization inhibitors. Preferred polymerization inhibitors are mixtures of an oxyl free radical-based polymerization inhibitor, a phenol-based polymerization inhibitor, and an amine-based polymerization inhibitor. Suitable examples are given in EP 2851402 A (FUJIFILM).

The polymerization inhibitor is preferably added at 200 to 20,000 ppm relative to the total amount of the inkjet ink.

Surfactants

The radiation curable inkjet ink may contain at least one surfactant. The surfactant can be anionic, cationic, non-ionic, or zwitter-ionic and is preferably added in a total quantity less than 3 wt % based on the total weight of the ink and particularly in a total less than 1.5 wt % based on the total weight of the radiation curable inkjet ink to prevent foaming of the ink in its container. The content of the surfactant is preferably 0.05 to 1.5 wt %, more preferably 0.10 to 1.0 wt % based on the total weight of the radiation curable inkjet ink.

Preferred surfactants are selected from fluoro surfactants (such as fluorinated hydrocarbons) and silicone surfactants. The silicone surfactants are preferably siloxanes and can be alkoxylated, polyester modified, polyether modified, polyether modified hydroxy functional, amine modified, epoxy modified and other modifications or combinations thereof. Preferred siloxanes are polymeric, for example polydimethylsiloxanes.

Preferred commercial silicone surfactants include BYK™ 333 and BYK™ UV3510 from BYK Chemie.

In a preferred embodiment, the surfactant is a polymerizable compound.

Preferred polymerizable silicone surfactants include a (meth)acrylated silicone surfactant. Most preferably the (meth)acrylated silicone surfactant is an acrylated silicone surfactant, because acrylates are more reactive than methacrylates.

In a preferred embodiment, the (meth)acrylated silicone surfactant is a polyether modified (meth)acrylated polydimethylsiloxane or a polyester modified (meth)acrylated polydimethylsiloxane.

Preferred commercially available (meth)acrylated silicone surfactants include: Ebecryl™ 350, a silicone diacrylate from Cytec; the polyether modified acrylated polydimethylsiloxane BYK™ UV3500 and BYK™ UV3530, the polyester modified acrylated polydimethylsiloxane BYK™ UV3570, all manufactured by BYK Chemie; Tego™ Rad 2100, Tego™ Rad 2200N, Tego™ Rad 2250N, Tego™ Rad 2300, Tego™ Rad 2500, Tego™ Rad 2600, and Tego™ Rad 2700, Tego™ RC711 from EVONIK; Silaplane™ FM7711, Silaplane™ FM7721, Silaplane™ FM7731, Silaplane™ FM0711, Silaplane™ FM0721, Silaplane™ FM0725, Silaplane™ TM0701, Silaplane™ TM0701T all manufactured by CHISSO Corporation; and DMS-R05, DMS-R11, DMS-R18, DMS-R22, DMS-R31, DMS-U21, DBE-U22, SIB1400, RMS-044, RMS-033, RMS-083, UMS-182, UMS-992, UCS-052, RTT-1011 and UTT-1012 all manufactured by GELEST Inc.

Preparation of Radiation Curable Inkjet Inks

The preparation of pigmented radiation curable inkjet inks is well-known to the skilled person. Preferred methods of preparation are disclosed in paragraphs [0076] to [0085] of WO 2011/069943 (AGFA).

Inkjet Printing Methods

An inkjet printing method according to a preferred embodiment of the invention includes the steps of: jetting one or more radiation curable inks as described above on a substrate; and UV curing the one or more curable inks on the substrate.

The UV curing is preferably performed by UV LEDs having an emission wavelength larger than 360 nm, preferably larger than 370 nm.

The radiation curable inkjet inks are jetted by one or more print heads ejecting small droplets in a controlled manner through nozzles onto a packaging substrate moving relative to the print head(s).

A preferred print head for the inkjet printing system is a piezoelectric head. Piezoelectric inkjet printing is based on the movement of a piezoelectric ceramic transducer when a voltage is applied thereto. The application of a voltage changes the shape of the piezoelectric ceramic transducer in the print head creating a void, which is then filled with inkjet ink or liquid. When the voltage is again removed, the ceramic expands to its original shape, ejecting a drop of ink from the print head.

A preferred piezoelectric print head is a so called push mode type piezoelectric print head, which has a rather large piezo-element capable of ejecting also high viscous inkjet ink droplets. Such a print head is available from RICOH as the GEN5s print head.

A preferred piezoelectric print head is a so-called through-flow piezoelectric drop-on-demand print head. Such a print head is available from TOSHIBA TEC as the CF1ou print head. Through-flow print heads are preferred because they enhance the reliability of food safe inkjet printing.

The inkjet print head normally scans back and forth in a transversal direction across the moving ink-receiver surface. Often the inkjet print head does not print on the way back. Bi-directional printing is preferred for obtaining a high areal throughput.

Another preferred printing method is by a "single pass printing process", which can be performed by using page wide inkjet print heads or multiple staggered inkjet print heads which cover the entire width of the ink-receiver surface. In a single pass printing process the inkjet print heads usually remain stationary and the ink-receiver surface is transported under the inkjet print heads.

In a particularly preferred embodiment, the inkjet printing of the UV curable inkjet inks is performed in a multi-pass printing mode. Multi-pass printing is a technique used to reduce banding in ink-jet printing. Dots of ink, when still in liquid form, tend to run together due to surface tension. This is referred to as coalescence. To print a high quality image, it is important to print individual round dots. But to achieve full saturated colours, the dots must overlap to completely cover the substrate. By only printing a portion of the image data so as to avoid simultaneously printing adjacent dots during each printing cycle, coalescence may be largely avoided. Additionally, by avoiding all horizontal adjacencies, the transverse speed of the printing mechanism can be increased up to two times the rated print speed of the print head. In a preferred embodiment, the number of passes used is to 2 to 6 passes, more preferably no more than 4 passes.

An advantage of using a multi-pass printing mode is that the UV curable inkjet inks are cured in consecutive passes, rather than in a single pass which would require a curing device with a high UV output. The print head lifetime is also larger for multi pass printing. While in single pass printing one side shooter is sufficient to replace the whole print head, in multi pass printing side shooters and even failings can be tolerated. Also the cost of a multi-pass printer is usually much lower, especially for wide format substrates.

Curing

The radiation curable inkjet inks are preferably cured by ultraviolet radiation.

In inkjet printing, the UV curing device may be arranged in combination with the print head of the inkjet printer, travelling therewith so that the UV curable inkjet ink is exposed to curing radiation very shortly after been jetted.

In such an arrangement it can be difficult to provide a small enough UV radiation source connected to and travelling with the print head. Therefore, a static fixed radiation source may be employed, e.g. a source of curing UV-light, connected to the radiation source by means of flexible radiation conductive means such as a fibre optic bundle or an internally reflective flexible tube.

Alternatively, the actinic radiation may be supplied from a fixed source to the radiation head by an arrangement of mirrors including a mirror upon the radiation head.

The source of radiation arranged not to move with the print head, may also be an elongated radiation source extending transversely across the ink-receiver surface to be cured and adjacent the transverse path of the print head so that the subsequent rows of images formed by the print head are passed, stepwise or continually, beneath that radiation source.

Any ultraviolet light source, as long as part of the emitted light can be absorbed by the photo-initiator or photo-initiator system, may be employed as a radiation source, such as, a high or low pressure mercury lamp, a cold cathode tube, a black light, an ultraviolet LED, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing.

UV radiation is generally classed as UV-A, UV-B, and UV-C as follows:
UV-A: 400 nm to 320 nm
UV-B: 320 nm to 290 nm
UV-C: 290 nm to 100 nm.

Furthermore, it is possible to cure the image using, consecutively or simultaneously, two light sources of differing wavelength or illuminance. For example, the first UV-source can be selected to be rich in UV-C, in particular in the range of 260 nm-200 nm. The second UV-source can then be rich in UV-A, e.g. a gallium-doped lamp, or a different lamp high in both UV-A and UV-B. The use of two UV-sources has been found to have advantages e.g. a fast curing speed and a high curing degree.

In a particularly preferred embodiment, the UV curing is performed using UV LEDs having an emission wavelength higher than 370 nm.

For facilitating curing, the inkjet printer often includes one or more oxygen depletion units. The oxygen depletion units place a blanket of nitrogen or other relatively inert gas (e.g. $CO_2$), with adjustable position and adjustable inert gas concentration, in order to reduce the oxygen concentration in the curing environment. Residual oxygen levels are usually maintained as low as 200 ppm, but are generally in the range of 200 ppm to 1200 ppm.

Manufacturing Methods of Indoor Decorative Articles

A method of manufacturing indoor decorative articles including the steps of:
a) inkjet printing one or more UV curable inkjet inks according to the invention as described above on a substrate; and b) UV curing the one or more UV curable inkjet inks. The UV curing is preferably performed using UV LEDs having an emission wave length larger than 360 nm.

In a preferred embodiment of the manufacturing method, the indoor decorative article is selected from the group consisting of decorative panels, furniture, wallpaper, doors, leather articles and textile fabrics.

Indoor Decorative Articles

An indoor decorative article including a cured layer of one or more radiation curable inkjet inks according to the present invention is preferably selected from the group consisting of decorative panels, furniture, wallpaper, doors leather articles, and textile fabrics.

The decorative panels may be simple panels, such as a glass or metal panel, but may also be decorative laminate panels selected from the group consisting of flooring panels, ceiling panels and wall panels. Decorative laminate panels are made by inkjet printing on a décor paper or a thermoplastic substrate which is then heat pressed together with at least a protective layer into a decorative laminate.

The thermoplastic substrate is preferably based on a material selected from the group consisting of polyvinyl-chloride (PVC), polypropylene (PP), polyethylene (PE), polyethylene-terephthalate (PET) and thermoplastic polyurethane (TPU) and combinations thereof. Decorative laminates based on PVC are also known in the market as LVT (Luxury Vinyl Tile).

The décor paper is impregnated by a thermosetting resin, like a melamin based thermosetting resin, before heat pressing. Such decorative laminate panels are known as wood based decorative laminate panels.

INDUSTRIAL APPLICABILITY

The radiation curable inkjet ink of the invention can also be advantageously used for other inkjet applications than manufacturing indoor decorative articles. There is no actual limitation on the type of inkjet application, but the radiation curable inkjet inks can also be advantageously used for packaging, for example, packaging for food, cosmetics and pharma.

The term "packaging for food, cosmetics or pharma" should be understood in its broadest meaning as encompassing a packaging of a substance intended for human or animal intake or administration. Food may be solid or liquid, for example, it encompasses also drinks like beer, soda, milk, vegetable oil, yoghourt and the like. There is also no limitation on the shape of the packaging for food, cosmetics or pharma. For example, food packaging may come in the shape of a cup, a bottle, a pouch, a box, a can, a carton, a wrapper and the like. Cosmetics encompass different solid or liquid products for cosmetical reasons that, for example, can be administered to human hair, such as a shampoo. Pharma packaging includes, for example, blister packaging, plastic bottles, pouches and bags for intravenous (IV) therapy.

Of course, for reasons of food safety and health, the composition of the radiation curable inkjet inks is preferably adapted to a so-called low migration ink composition.

In a preferred embodiment, the radiation curable inkjet inks include a monomer including at least one acrylate group and at least one ethylenically unsaturated polymerizable group selected from the group consisting of allylether, allylester, allylcarbonate, vinyl ether, vinylester, vinylcarbonate, fumarate, and maleate. Preferred examples of such monomers are disclosed in EP 2053103 A (AGFA).

The radiation curable inkjet ink preferably includes a vinylether acrylate monomer represented by Formula (VA-1) disclosed above.

The radiation curable inkjet ink most preferably includes VEEA as vinylether acrylate monomer.

In a preferred embodiment, the vinylether(meth)acrylate monomer is present in the free radical curable inkjet ink in an amount of 20 wt % to 90 wt %, more preferably 25 wt % to 80 wt % and most preferably 30 wt % to 70 wt %, all based upon the total weight of the radiation curable inkjet ink.

In a particularly preferred embodiment, the polymerizable composition of the radiation curable inkjet ink consists essentially of: a) 25-100 wt % of one or more polymerizable compounds A having at least one acrylate group and at least one vinyl ether group; b) 0-55 wt % of one or more polymerizable compounds B selected from the group consisting of monofunctional acrylates and difunctional acrylates; and c) 0-55 wt % of one or more polymerizable compounds C selected from the group consisting of trifunctional acrylates, tetrafunctional acrylates, pentafunctional acrylates and hexafunctional acrylates, with the proviso that if the weight percentage of compounds B>24 wt %, then the weight percentage of compounds C>1 wt %; and wherein all weight percentages of A, B and C are based upon the total weight of the polymerizable composition; and with the proviso that at least one polymerizable-compound B or C is present in the polymerizable composition if the radiation curable inkjet ink contains no initiator. If no initiator is present the radiation curable inkjet inks may be cured by electron beam curing.

EXAMPLES

Materials

All materials used in the following examples were readily available from standard sources such as Aldrich Chemical Co. (Belgium) and Acros (Belgium) unless otherwise specified. The water used was demineralized water.

PIG-C is an abbreviation used for Hostaperm™ Blue P-BFS, a C.I. Pigment Blue 15:4 pigment from CLARIANT.

PIG-M is a mixed crystal of quinacridones available as Cinquasia™ Magenta D 4500 J from BASF.

PIG-Y is a C.I. Pigment Yellow 150 pigment for which Cromophtal™ Yellow D1085 from BASF was used.

PIG-K is an abbreviation used for Special Black™ 550, which is a carbon black available from EVONIK.

SYN is the dispersion synergist according to Formula (A):

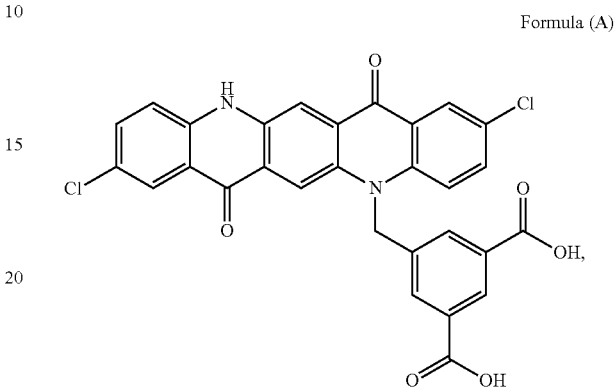

Formula (A)

and was synthesized in the same manner as described in Example 1 of WO 2007/060254 (AGFA GRAPHICS) for the synergist QAD-3.

DB162 is an abbreviation used for the polymeric dispersant Disperbyk™ 162 available from BYK CHEMIE GMBH whereof the solvent mixture of 2-methoxy-1-methylethylacetate, xylene and n-butylacetate was removed. The polymeric dispersant is a polyester-polyurethane dispersant on the basis of caprolacton and toluene diisocyanate having an amine value of 13 mg KOH/g, a Mn of about 4,425 and a Mw of about 6,270.

DPGDA is dipropyleneglycoldiacrylate available as Laromer™ DPGDA from BASF.

G1122 is a monofunctional urethane acrylate available as Genomer™ 1122 from RAHN.

TBCH is 4-tert.butylcyclohexylacrylate available under the trade name of Sartomer™ CD217 from ARKEMA.

VEEA is 2-(2'-vinyloxyethoxy)ethyl acrylate, a difunctional monomer available from NIPPON SHOKUBAI, Japan.

NVC is N-vinyl caprolactam available from BASF BELGIUM, NV.

TEGDVE is triethyleneglycol divinylether from BASF.

SR789 is 2-Propenoic acid, (octahydro-4,7-methano-1H-inden-5-yl)methyl ester (CASRN127823-21-6) available as Sartomer™ SR789 from ARKEMA.

MPDA is 3-methyl-1,6-pentanediyldiacrylate available as Sartomer™ SR341 from ARKEMA.

15EO-TMPTA is an ethoxylated (15) trimethylolpropane triacrylate containing fifteen ethoxy units having a molecular weight of 956 and available as Sartomer™ SR9035 from ARKEMA.

ITX is Darocur™ ITX is an isomeric mixture of 2- and 4-isopropyl thioxanthone from BASF.

TPO-L is ethyl phenyl(2,4,6-trimethylbenzoyl)phosphinate available as Omnirad™ TPO-L from IGM Resins BV.

BAPO is a bis(2,4,6-trimethylbenzoyl)-phenylphosphineoxide photoinitiator available as Irgacure™ 819 from BASF.

TX-1 is a polymerizable thioxanthone having the chemical structure TX-1 and being a 50 w % solution in VEEA. THIOXANTHON-1 can be prepared according to Example 1 of EP 2684876 A (AGFA).

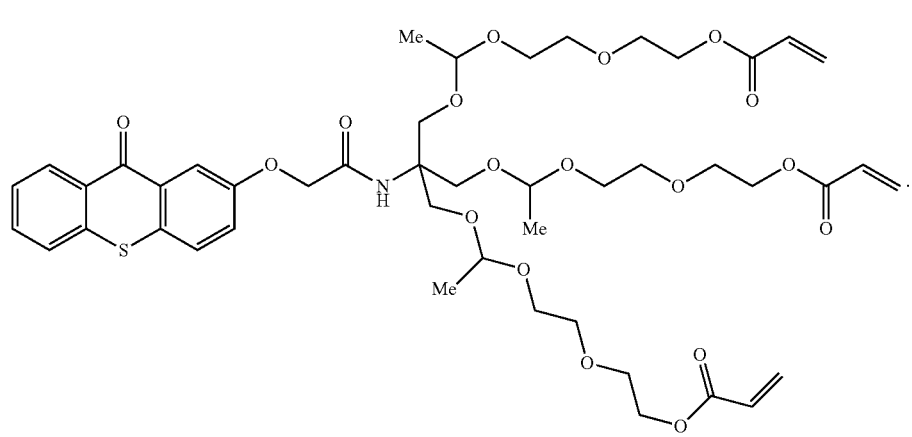

TX-1

CN3755 is an acrylated amine synergist available as Sartomer™ CN 3755 from ARKEMA.

GAB is a polymeric 4-dimethylaminobenzoic acid derivative available as GENOPOL™ AB2 from RAHN.

Stabi I is a monomeric carbodiimide available as Stabaxol™ I from LANXESS AG.

Stabi L is a monomeric carbodiimide available as Stabaxol™ L from LANXESS AG.

Stabi Q1 is the following compound:

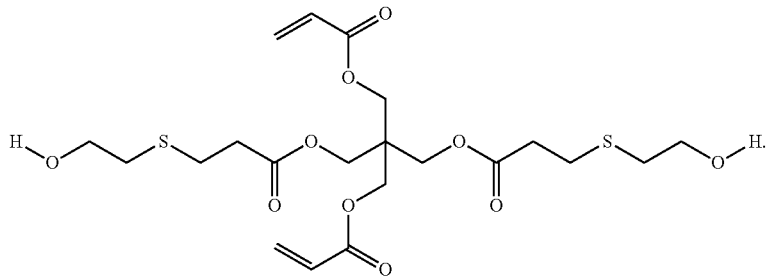

and was synthesized as follows:

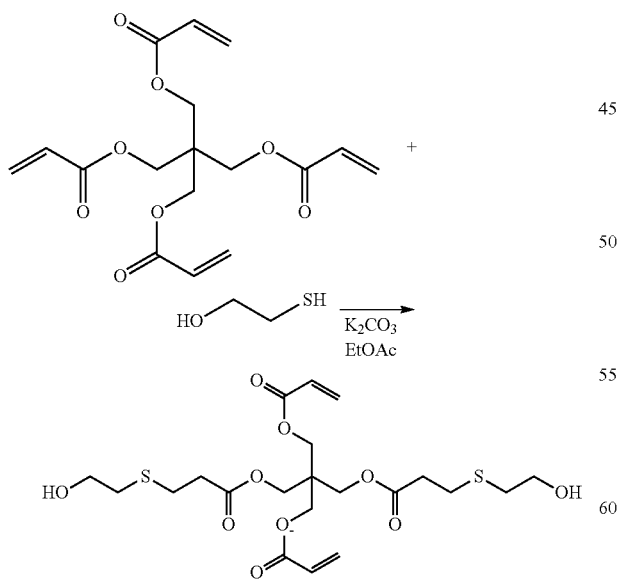

as part of a mixture of Michael addition products 105.7 g (0.3 mol) pentaerythritol tetraacrylate was dissolved in 450 ml ethyl acetate. 0.44 g BHT and 20.7 g (0.15 mol) potassium carbonate were added and the mixture was stirred at room temperature. A solution of 46.8 g (0.6 mol) 2-mercapto-ethanol in 150 ml ethylacetate was added and the mixture was refluxed for four and a half hour. The mixture was allowed to cool down to room temperature. The potassium carbonate was removed by filtration and the solvent was removed under reduced pressure. 150 g of a mixture of Michael addition products was isolated as a viscous oil. Stabi Q1 was characterized using LC-MS and found to be a complex mixture of thio-ethers based on a combination of Michael addition reactions and transesterification reactions. The mixture was used in ink formulations without purification.

Stabi Q2 is the following compound:

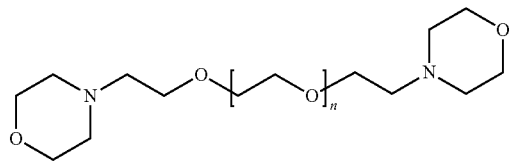

n = 9 on average and was synthesized as follows:

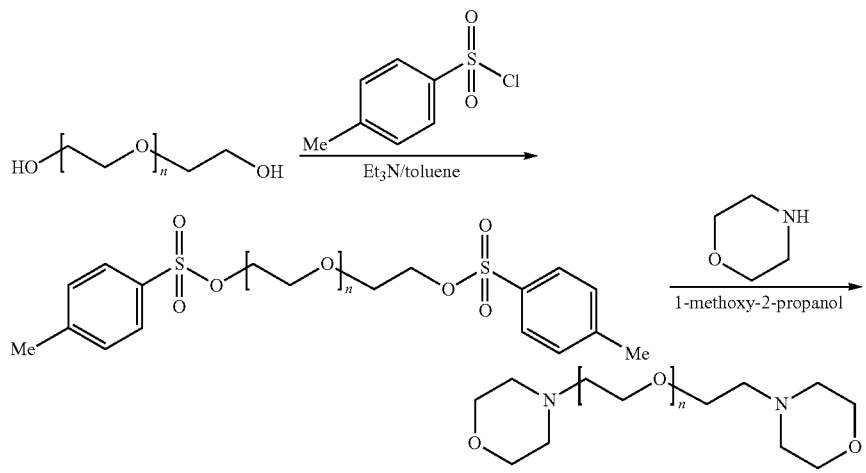

200 g (0.5 mol) poly(ethylene glycol) 400 was dissolved in 1 liter toluene. 190 g (1 mol) tosyl chloride was added followed by the dropwise addition of a solution of 101 g (139 ml, 1 mol) triethyl amine in 850 ml toluene. The reaction was allowed to continue for-18 hours at room temperature. The precipitated hydrochloric acid salt of triethyl amine was removed by filtration and the solvent was removed under reduced pressure. 347 g of the tosylated poly(ethylene glycol) was isolated and used without further purification.

28.4 g (0.04 mol) of the tosylated poly(ethylene glycol) was dissolved in 500 ml 1-methoxy-2-propanol. 10.45 g (0.12 mol) morpholine was added and the mixture was refluxed for 16 hours. The reaction mixture was allowed to cool down to room temperature and the solvent was removed under reduced pressure. 500 ml ethyl acetate was added to the residue. The precipitated salts were removed by filtration and the filtrate was treated with Lewatit M600 MB (Bayer AG), activated with sodium hydroxide. The ion exchanger was removed by filtration and the solvent was evaporated under reduced pressure. 10.65 g of the morpholine functionalized poly(ethylene glycol) was isolated (TLC analysis on TLC Silica gel 60F$_{254}$, eluent methylene chloride/methanol 85/15, R$_f$: 0.39)

SOQ-MIX is a mixture of singlet oxygen quenchers and was synthesized as follows. 33.94 g (0.2 mol) 2-mercapto-ethyl-diethylamine chlorohydrate was dissolved in 200 ml ethanol. 82 g of a 21 w % solution of sodium ethanolate in ethanol (0.21 mol) was added and the mixture was stirred at room temperature for 30 minutes. 0.44 g BHT was added followed by the addition of a solution of 35.2 g (0.1 mol) pentaerythritol tetra-acrylate in 200 ml ethanol. The reaction was allowed to continue for 4 hours at room temperature. 300 ml ethyl acetate/hexane 1/1 was added and the precipitated salts were removed by filtration. The solvent mixture was evaporated under reduced pressure and the residue was treated with 300 ml ethyl acetate. The precipitated salts were removed by filtration and the solvent was evaporated under reduced pressure. The mixture was analyzed using LC MS. The following compounds were, based on mass spectroscopy, identified as main components in a complex mixture. The complex mixture contained the singlet oxygen quencher S-1 as main component:

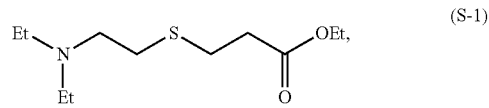 [SMILES: CCOC(=O)CCSCCN(CC)CC]

(S-1)

along with other singlet oxygen quenchers S-2 to S-5:

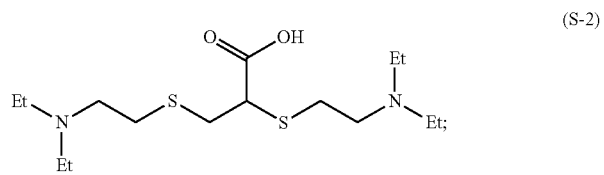

(S-2)

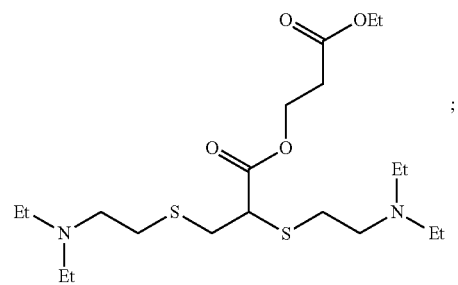

(S-3)

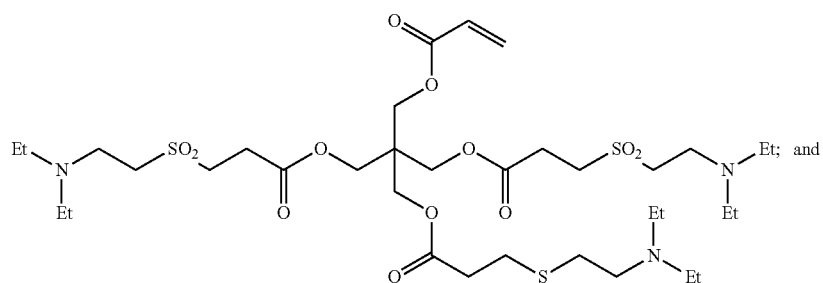

(S-4)

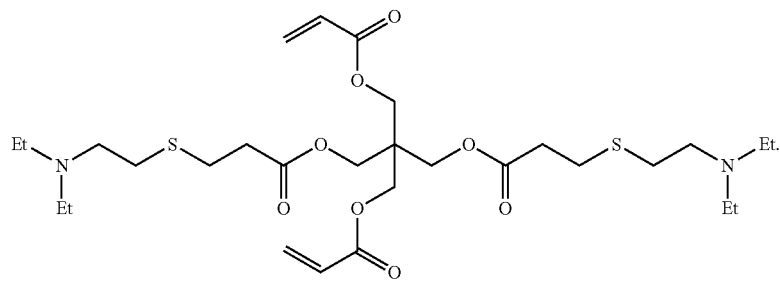

(S-5)

The mixture also contained some impurities like:

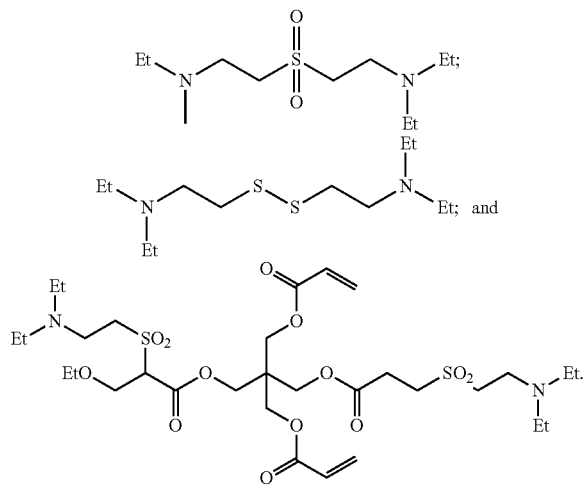

It is obvious for the one skilled in the art that isomeric structures thereof may also be present.

MSOQ-1 n4 is a singlet oxygen quencher according MSOQ-1 wherein n=4 and was synthesized as follows:

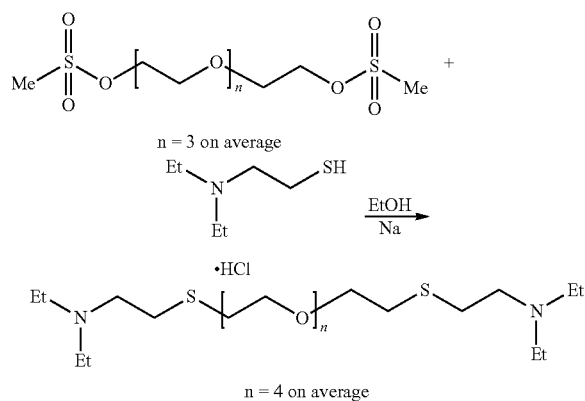

Sodium ethanolate was freshly prepared by adding 49.6 g (2.16 mol) sodium portionwise to 840 ml ethanol. The mixture was stirred for three hours. 183 g (1.08 mol) 2-(diethylamino)ethanethiol hydrochloride was added and the mixture was stirred for 30 minutes. A solution of 150 g of dimesylated poly(ethylene glycol) 200 in 400 ml ethanol was added. The reaction mixture was heated to reflux for 4 hours. The reaction mixture was allowed to cool down to room temperature, the precipitated salts were removed by filtration and the solvent was evaporated under reduced pressure. The residue was dissolved in 600 ml methylene chloride and carefully extracted three times with 240 ml 10% hydrochloric acid. The aqueous phase was neutralized with a 30 w % sodium hydroxide solution and extracted three times with 360 ml methylene chloride. The pooled methylene chloride fractions were dried over $Na_2SO_4$ and evaporated under reduced pressure. The crude polymer was purified by preparative column chromatography on silicagel, using methylene chloride/methanol/ammonia 90/9/1 as eluent. 125 g of MSOQ-1n4 was isolated.

MSOQ-13 was synthesized according the following scheme:

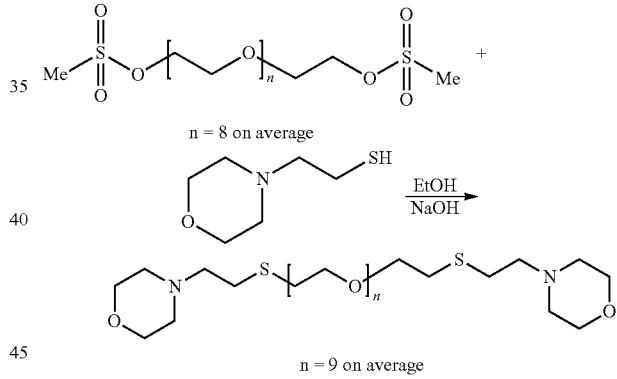

The synthesis of mesylated poly(ethylene glycol)s has been described by Grieshaber at al. (Macromolecules, 42(7), 2532-2541 (2009)). 1-(2-mercaptoethyl) morpholine was prepared according to WO 2012/075494 (S).

A solution of 142 g (3.55 mol) sodium hydroxide in 1.5 liter ethanol was prepared. 521.8 g (3.55 mol) 1-(2-mercaptoethyl)piperidine was added, followed by the addition of 809 g of dimesylated poly(ethylene glycol) 400 over 30 minutes, while keeping the temperature below 35° C. The reaction was allowed to continue for two hours at room temperature. The precipitated salts were removed by filtration and washed with 1 liter ethanol. The combined ethanol fractions were evaporated under reduced pressure and the residue was redissolved in 750 ml methylene chloride. The methylene chloride solution was extracted three times with 200 ml 5N NaOH, once with 200 ml water and dried over $MgSO_4$. The methylene chloride was removed under reduced pressure and 600 g of MSOQ-13 was isolated.

SOQ-1n9 is a singlet oxygen quencher according MSOQ-1 wherein n=9 and was synthesized as follows:

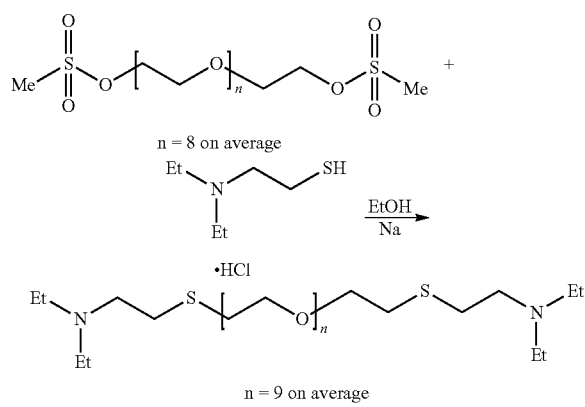

Sodium ethanolate was freshly prepared by adding 28.5 g (1.239 mol) sodium portionwise to 480 ml ethanol. The mixture was stirred for three hours. 105 g (0.627 mol) 2-(diethylamino)ethanethiol hydrochloride was added and the mixture was stirred for 30 minutes. A solution of 140.2 g of dimesylated poly(ethylene glycol) 400 in 250 ml ethanol was added. The reaction mixture was heated to reflux for 4 hours. The reaction mixture was allowed to cool down to room temperature, the precipitated salts were removed by filtration and the solvent was evaporated under reduced pressure. The crude polymer was purified by preparative column chromatography on silicagel, using methylene chloride/methanol/ammonia 90/9/1 as eluent. 97 g of MSOQ-1n9 was isolated.

INHIB is a mixture forming a polymerization inhibitor having a composition according to Table 3.

TABLE 3

| Component | wt % |
|---|---|
| VEEA | 82.4 |
| p-methoxyphenol | 4.0 |
| Butylated hydroxytoluene (BHT) | 10.0 |
| Cupferron ™ AL | 3.6 |

Cupferron™ AL is aluminum N-nitrosophenylhydroxylamine from WAKO CHEMICALS LTD.

C7500 is a silicone surfactant available as Silwet™ L7500 from OSI SPECIALTIES BENELUX NV PET175 is a 175 μm thick unsubbed polyethylene terephthalate sheet available as Astera™ type UR175.334 from AGFA-GEVAERT NV.

Measurement Methods

1. Formaldehyde Emission

A UV curable ink was printed with a Anapurna™ H2050i LED inkjet system to 100% ink coverage on an aluminium substrate of 25 cm$^2$ and UV cured. Then 5 strips of 1×5 cm are cut from the printed aluminium sample and brought into a gaschromatography vial of 20 ml. The closed vial is heated for 60 minutes at 100° C. Immediately after the heating, the hot air is collected and fed into a cartridge (Xposure Aldehyde Sampler from WATERS) containing acidified 2,4-dinitrophenyl hydrazine coated silica. Another 180 ml of pure air is fed into the cartridge through the sample vial to ensure that all formaldehyde is loaded in the cartridge. The amount of formaldehyde is determined by HPLC-DAD from the amount of the reaction product formaldehyde, 2-(2,4-dinitrophenyl) hydrazon eluted from the cartridge. The content is determined based on a calibration curve established with a standard solution of formaldehyde, 2-(2,4-dinitrophenyl) hydrazon.

2. Acetaldehyde Emission

A UV curable ink was printed with a Anapurna™ H2050i LED inkjet system to 100% ink coverage on an aluminium substrate of 25 cm$^2$ and UV cured. Then 5 strips of 1×5 cm are cut from the printed aluminium sample and brought into a gaschromatography vial of 20 ml. The closed vial is heated for 120 minutes at 100° C. After cooling to 25° C., the air of the closed vial is collected and fed into a cartridge (Xposure Aldehyde Sampler from WATERS) containing acidified 2,4-dinitrophenyl hydrazine coated silica. Another 180 ml of pure air is fed into the cartridge through the sample vial to ensure that all acetaldehyde is loaded in the cartridge. The amount of acetaldehyde is determined by HPLC-DAD from the amount of the reaction product acetaldehyde, 2-(2,4-dinitrophenyl) hydrazon eluted from the cartridge. The content is determined based on a calibration curve established with a standard solution of acetaldehyde, 2-(2,4-dinitrophenyl) hydrazon.

3. Smell Test

The samples were evaluated for smell by a panel of five persons, scoring each sample from 0 for complete odourless to 5 for a very persistent smell. The five scores were averaged to deliver an averaged smell score between and 5. For a good performance, the averaged smell score should be as small as possible and not more than 3.

4. Average Particle Size

The average particle size of pigment particles in a pigment dispersion was determined by photon correlation spectroscopy at a wavelength of 633 nm with a 4 mW HeNe laser on a diluted sample of the pigmented inkjet ink. The particle size analyzer used was a Malvern™ nano-S available from Goffin-Meyvis.

The sample was prepared by addition of one drop of dispersion to a cuvette containing 1.5 mL ethyl acetate and mixed until a homogenous sample was obtained. The measured particle size is the average value of 3 consecutive measurements consisting of 6 runs of 20 seconds.

5. Surface Tension

The static surface tension of the UV curable inks was measured with a KRÜSS tensiometer K9 from KRÜSS GmbH, Germany at 25° C. after 60 seconds.

6. Viscosity

The viscosity of the UV curable compositions was measured at 45° C. and at a shear rate of 1,000 s$^{-1}$ using a Rotovisco™ RV1 viscometer from HAAKE.

7. TLC

The molecular mass was determined using TLC-MS, according to the following procedure. A TLC was run under circumstances given in the synthetic examples. The TLC was analyzed using a CAMAG TLC-MS interface coupled to an AmaZon SL mass spectrometer (supplied by Brüker Daltonics) via an Agilent 1100 HPLC pump. First a blank spectrum was taken by eluting a spot on the TLC plate where no compounds are present with a 0.01 molar solution of ammonium acetate in methanol. A second spectrum of the compound to be analyzed was taken by eluting the spot of the compound under consideration with a 0.01 molar solution of ammonium acetate in methanol. The first spectrum was subtracted from the second spectrum, giving the spectrum of the compound to be analyzed.

Example 1

This Example illustrates the reduction in formaldehyde emission from UV cured layers of radiation curable inkjet inks in accordance with the invention.

Preparation of Magenta Dispersion DISP-M

A dispersion was made by mixing the components according to Table 4 for 30 minutes using a DISPERLUX™ disperser from DISPERLUX S.A.R.L., Luxembourg. The dispersion was then milled using a Bachofen DYNOMILL ECM mill filled with 0.4 mm yttrium stabilized zirconia beads ("high wear resistant zirconia grinding media" from TOSOH Co.). The mixture was circulated over the mill for 2 hours. After milling, the concentrated pigment dispersion was discharged over a 1 μm filter into a vessel. The resulting concentrated pigment dispersion DISP-M had an average particle size of 128 nm.

TABLE 4

| Component | wt % |
|---|---|
| PIG-M | 16.94 |
| SYN | 0.90 |
| DB162 | 16.94 |
| INHIB | 1.00 |
| DPGDA | 64.22 |

Preparation of Radiation Curable Inkjet Inks

The above prepared magenta pigment dispersion DISP-M was then used to prepare the comparative UV curable inkjet inks COMP-1 to COMP-11 and the inventive UV curable inkjet inks INV-1 to INV-8 according to Table 5 to Table 7. The wt % is based on the total weight of the inkjet ink.

TABLE 5

| wt % of: | COMP-1 | COMP-2 | COMP-3 | COMP-4 | COMP-5 | COMP-6 |
|---|---|---|---|---|---|---|
| DISP-M | 26.56 | 26.56 | 26.56 | 26.56 | 26.56 | 26.56 |
| ITX | 2.95 | 2.95 | 2.95 | 2.95 | 2.95 | 2.95 |
| TPO L | 4.50 | 4.50 | 4.50 | 4.50 | 4.50 | 4.50 |
| BAPO | 3.50 | 3.50 | 3.50 | 3.50 | 3.50 | 3.50 |
| CN3755 | 4.00 | 4.00 | 4.00 | 4.00 | 4.00 | 4.00 |
| DPGDA | 3.40 | 3.40 | 3.40 | 3.40 | 3.40 | 3.40 |
| G1122 | 3.76 | 3.76 | 3.76 | 3.76 | 3.76 | 3.62 |
| TBCH | 18.90 | 18.90 | 18.90 | | | |
| VEEA | 30.69 | 28.69 | 28.69 | | | |
| TEGDVE | | | | 10.00 | | |
| SR789 | | | | 8.90 | 18.90 | 18.19 |
| MPDA | | | | 30.69 | 30.69 | 29.54 |
| Stabi I | | 2.00 | | | | 2.00 |
| Stabi L | | | 2.00 | | | |
| INHIB | 0.74 | 0.74 | 0.74 | 0.74 | 0.74 | 0.74 |
| C7500 | 1.00 | 1.00 | 1.00 | 1.00 | 1.00 | 1.00 |

TABLE 6

| wt % of: | COMP-7 | COMP-8 | COMP-9 | COMP-10 | COMP-11 |
|---|---|---|---|---|---|
| DISP-M | 26.56 | 26.56 | 26.56 | 26.56 | 26.56 |
| ITX | 2.95 | | | | |
| TPO L | 4.50 | 4.50 | 4.50 | 4.50 | 4.50 |
| BAPO | 3.50 | 3.50 | 3.50 | 3.50 | 3.50 |
| CN3755 | 4.00 | 4.00 | 4.00 | 4.00 | 4.00 |
| DPGDA | 3.40 | 3.40 | 3.40 | 3.40 | 3.40 |
| G1122 | 3.62 | 6.71 | 6.41 | 6.11 | 6.41 |
| TBCH | | 18.90 | 18.07 | 17.23 | 18.07 |
| VEEA | | 30.69 | 29.33 | 27.97 | 29.32 |
| SR789 | 18.19 | | | | |
| MPDA | 29.54 | | | | |
| Stabi L | 2.00 | | | | |
| Stabi Q1 | | | 2.50 | 5.00 | |
| Stabi Q2 | | | | | 2.50 |
| INHIB | 0.74 | 0.74 | 0.74 | 0.74 | 0.74 |
| C7500 | 1.00 | 1.00 | 1.00 | 1.00 | 1.00 |

TABLE 7

| wt % of: | INV-1 | INV-2 | INV-3 | INV-4 | INV-5 | INV-6 | INV-7 | INV-8 |
|---|---|---|---|---|---|---|---|---|
| DISP-M | 26.56 | 26.56 | 26.56 | 26.56 | 26.56 | 26.56 | 26.56 | 26.56 |
| ITX | | | 2.95 | | | | | |
| TPO L | 4.50 | 4.50 | 4.50 | 4.50 | 4.50 | 4.50 | 4.50 | 4.50 |
| BAPO | 3.50 | 3.50 | 3.50 | 3.50 | 3.50 | 3.50 | 3.50 | 3.50 |
| CN3755 | 4.00 | 4.00 | 4.00 | 4.00 | 4.00 | 4.00 | 4.00 | 4.00 |
| DPGDA | 3.40 | 3.40 | 3.40 | 3.40 | 3.40 | 3.40 | 3.40 | 3.40 |

TABLE 7-continued

| wt % of: | INV-1 | INV-2 | INV-3 | INV-4 | INV-5 | INV-6 | INV-7 | INV-8 |
|---|---|---|---|---|---|---|---|---|
| G1122 | 6.41 | 6.11 | 5.76 | 6.41 | 6.11 | 6.11 | 6.41 | 6.11 |
| TBCH | 18.07 | 17.23 | 16.24 | 18.07 | 17.23 | 17.23 | 18.07 | 17.23 |
| VEEA | 29.32 | 27.96 | 26.35 | 29.32 | 27.96 | 27.96 | 29.32 | 27.96 |
| SOQ-MIX | 2.50 | 5.00 | 5.00 | | | | | |
| MSOQ-1n4 | | | | 2.50 | 5.00 | | | |
| MSOQ-13 | | | | | | 5.00 | | |
| MSOQ-1n9 | | | | | | | 2.50 | 5.00 |
| INHIB | 0.74 | 0.74 | 0.74 | 0.74 | 0.74 | 0.74 | 0.74 | 0.74 |
| C7500 | 1.00 | 1.00 | 1.00 | 1.00 | 1.00 | 1.00 | 1.00 | 1.00 |

Evaluation and Results

TABLE 8

| Ink | ITX | Vinylether compound | Singlet Oxygen Quencher Type | Singlet Oxygen Quencher Amount (mmol) | Formaldehyde ($\mu g/m^2$) |
|---|---|---|---|---|---|
| COMP-1 | Yes | VEEA | None | — | 441 |
| COMP-2 | Yes | VEEA | Stabi I | 6 | 471 |
| COMP-3 | Yes | VEEA | Stabi L | 4 | 429 |
| COMP-4 | Yes | DVE | None | — | 172 |
| COMP-5 | Yes | No | None | — | 16 |
| COMP-6 | Yes | No | Stabi I | 6 | 17 |
| COMP-7 | Yes | No | Stabi L | 4 | 15 |
| COMP-8 | No | VEEA | None | — | 17 |
| COMP-9 | No | VEEA | Stabi Q1 | 5 | 21 |
| COMP-10 | No | VEEA | Stabi Q1 | 10 | 34 |
| COMP-11 | No | VEEA | Stabi Q2 | 13 | 15 |
| INV-1 | No | VEEA | SOQ-MIX | 4 | 0 |
| INV-2 | No | VEEA | SOQ-MIX | 8 | 0 |
| INV-3 | Yes | VEEA | SOQ-MIX | 8 | 6 |
| INV-4 | No | VEEA | MSOQ-1n4 | 6 | 0 |
| INV-5 | No | VEEA | MSOQ-1n4 | 12 | 0 |
| INV-6 | No | VEEA | MSOQ-13 | 16 | 4 |
| INV-7 | No | VEEA | MSOQ-1n9 | 9 | 0 |
| INV-8 | No | VEEA | MSOQ-1n9 | 17 | 0 |

From Table 8, it should be clear that the formaldehyde released by UV cured layers of inkjet inks INV-1 to INV-8 in accordance with the invention is minimized.

Example 2

This Example illustrates the reduction in formaldehyde emission by using a UV curable CMYK inkjet ink set in accordance with the invention.

Preparation of Pigment Dispersions

Preparation of Cyan Pigment Dispersion DISP-C

A dispersion was made by mixing the components according to Table 9 for 30 minutes using a DISPERLUX™ disperser from DISPERLUX S.A.R.L., Luxembourg. The dispersion was then milled using a Bachofen DYNOMILL ECM mill filled with 0.4 mm yttrium stabilized zirconia beads ("high wear resistant zirconia grinding media" from TOSOH Co.). The mixture was circulated over the mill for 2 hours. After milling, the concentrated pigment dispersion was discharged over a 1 μm filter into a vessel. The resulting concentrated pigment dispersion DISP-C had an average particle size of 97 nm.

TABLE 9

| Component | wt % |
|---|---|
| PIG-C | 12.00 |
| DB162 | 12.00 |

TABLE 9-continued

| Component | wt % |
|---|---|
| INHIB | 1.00 |
| DPGDA | 75.00 |

Preparation of Yellow Pigment Dispersion DISP-Y

A dispersion was made by mixing the components according to Table 10 for 30 minutes using a DISPERLUX™ disperser from DISPERLUX S.A.R.L., Luxembourg. The dispersion was then milled using a Bachofen DYNOMILL ECM mill filled with 0.4 mm yttrium stabilized zirconia beads ("high wear resistant zirconia grinding media" from TOSOH Co.). The mixture was circulated over the mill for 2 hours. After milling, the concentrated pigment dispersion was discharged over a 1 μm filter into a vessel. The resulting concentrated pigment dispersion DISP-Y had an average particle size of 112 nm.

TABLE 10

| Component | wt % |
|---|---|
| PIG-Y | 16.77 |
| DB162 | 16.77 |
| INHIB | 1.00 |
| DPGDA | 67.00 |

Preparation of Black Pigment Dispersion DISP-K

A dispersion was made by mixing the components according to Table 11 for 30 minutes using a DISPERLUX™ disperser from DISPERLUX S.A.R.L., Luxembourg. The dispersion was then milled using a Bachofen DYNOMILL ECM mill filled with 0.4 mm yttrium stabilized zirconia beads ("high wear resistant zirconia grinding media" from TOSOH Co.). The mixture was circulated over the mill for 2 hours. After milling, the concentrated pigment dispersion was discharged over a 1 μm filter into a vessel. The resulting concentrated pigment dispersion DISP-K had an average particle size of 103 nm.

TABLE 11

| Component | wt % |
|---|---|
| PIG-K | 10.83 |
| PIG-C | 3.91 |
| PIG-M | 2.03 |
| SYN | 0.11 |
| DB162 | 16.72 |
| INHIB | 1.00 |
| DPGDA | 65.40 |

Preparation of UV Curable CMYK Inkjet Ink Sets

The magenta pigment dispersion DISP-M from Example 1 and the pigment dispersions DISP-C, DISP-Y and DISP-K were used to prepare the CMYK Inkjet Ink Set A according to Table 12 and the CMYK Inkjet Ink Set B according to Table 13. The wt % is based on the total weight of the inkjet ink.

TABLE 12

| wt % of | C | M | Y | K |
|---|---|---|---|---|
| PIG-C | 2.50 | — | — | 0.58 |
| PIG-M | — | 4.50 | — | 0.30 |
| PIG-Y | — | — | 2.50 | — |
| PIG-K | — | — | — | 1.60 |
| SYN | — | 0.24 | — | 0.02 |
| DB162 | 2.50 | 4.50 | 2.50 | 2.47 |
| DPGDA | 23.12 | 20.46 | 16.11 | 15.64 |
| 15EO-TMPTA | 3.00 | 0.00 | 4.00 | 2.00 |
| VEEA | 25.60 | 30.69 | 29.86 | 30.05 |
| G1122 | 13.00 | 6.71 | 9.94 | 8.61 |
| TBCH | 14.03 | 18.90 | 16.84 | 17.24 |
| TPO-L | 4.50 | 4.50 | 4.50 | 4.50 |
| ITX | 0.00 | 0.00 | 2.00 | 5.00 |
| BAPO | 2.25 | 3.50 | 2.25 | 2.00 |
| CN3755 | 7.50 | 4.00 | 7.50 | 8.00 |
| SOQ-7 | — | — | — | — |
| C7500 | 1.00 | 1.00 | 1.00 | 1.00 |
| INHIB | 1.00 | 1.00 | 1.00 | 1.00 |

TABLE 13

| wt % of | C | M | Y | K |
|---|---|---|---|---|
| PIG-C | 2.50 | — | — | 0.58 |
| PIG-M | — | 4.50 | — | 0.30 |
| PIG-Y | — | — | 2.50 | — |
| PIG-K | — | — | — | 1.60 |
| SYN | — | 0.24 | — | 0.02 |
| DB162 | 2.50 | 4.50 | 2.50 | 2.47 |
| DPGDA | 23.12 | 20.46 | 16.11 | 15.64 |
| 15EO-TMPTA | 3.00 | 0.00 | 4.00 | 2.00 |
| VEEA | 23.17 | 27.97 | 27.22 | 28.58 |
| G1122 | 11.77 | 6.11 | 9.06 | 7.84 |
| TBCH | 12.70 | 17.23 | 15.35 | 15.70 |
| TPO-L | 4.50 | 4.50 | 4.50 | 4.50 |
| ITX | 0.00 | 0.00 | 2.00 | 5.00 |
| BAPO | 2.25 | 3.50 | 2.25 | 2.00 |
| CN3755 | 7.50 | 4.00 | 7.50 | 8.00 |
| SOQ-7 | 5.00 | 5.00 | 5.00 | 3.79 |
| C7500 | 1.00 | 1.00 | 1.00 | 1.00 |
| INHIB | 1.00 | 1.00 | 1.00 | 1.00 |

Evaluation and Results

The viscosity for all inkjet inks of CMYK ink sets A and B was determined and found to be between 10 and 12 mPa·s at 45° C.

The surface tension for all inkjet inks of CMYK ink sets A and B was determined and found to be between 29 and 31 mN/m at 25° C.

The CMYK ink sets A and B were used to print an identical multicolour image on an aluminium substrate of 25 cm² with a Anapurna™ H2050i LED inkjet system available from AGFA NV.

The printed samples were then tested on formaldehyde emission with the above described analytical procedure. The analytical results are given in Table 14.

TABLE 14

| Sample printed with | Detected Formaldehyde |
|---|---|
| CMYK Inkjet Ink Set A | 125 μg/m² |
| CMYK Inkjet Ink Set B | 3 μg/m² |

The results in Table 14 clearly show that the CMYK Inkjet Ink Set B in accordance with the invention produces far less formaldehyde than the comparative CMYK Inkjet Ink Set B. The CMYK Inkjet Ink Set B is suitable for indoor decoration, while the CMYK Inkjet Ink Set B is not.

Example 3

This Example illustrates the reduction in bad smell from UV cured radiation curable inkjet inks further containing a polymerizable acyl phosphine oxide initiator.

Preparation of Polymerizable Acylphosphine Oxide

The synthesis is performed in steps 1 to 5.

Step 1: Synthesis of Compound C-2

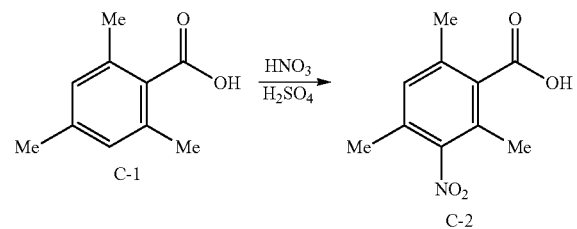

100 g (0.6 mol) of 2,4,6-trimethyl-benzoic acid (compound C-1) was added to 2.79 kg nitric acid (65 w %). 116.6 ml concentrated sulfuric acid was added and the mixture was stirred for 18 hours at room temperature. The mixture was added to 1.5 kg of an ice/water mixture. 2,4,6-trimethyl-3-nitro-benzoic acid (compound C-2) precipitated from the medium. Compound C-2 was isolated by filtration and washed to neutral pH with water. The isolated compound C-2 was dried to constant weight. 112 g 2,4,6-trimethyl-3-nitro-benzoic acid (yield: 89%) was isolated (m.p. 194° C. (lit. 184° C. Chemische Berichte, V120(5), P803-9 (1987))).

Step 2: Synthesis of Compound C-3

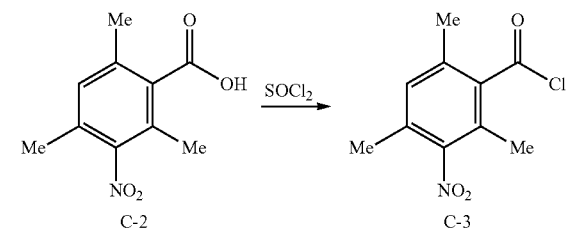

112 g (0.53 mol) of 2,4,6-trimethyl-3-nitro-benzoic acid was suspended in 1.2 l toluene. 63.28 g (0.8 mol) pyridine was added followed by the addition of 95.18 g (0.8 mol) thionyl chloride over 30 minutes. The temperature rose to 36° C. during the addition. The reaction was allowed to continue for an hour at room temperature. The precipitated salts were removed by filtration and the solvent was evaporated under reduced pressure. 500 ml methyl t.butyl ether was added and the mixture was evaporated again under reduced pressure. This was repeated for a second time. 119 g of 2,4,6-trimethyl-3-nitro-benzoyl chloride (yield: 99%) was isolated. The compound C-3 was used in the next step without further purification.

Step 3: Synthesis of Compound C-4

The compound C-4 is (3-nitro-2,4,6-trimethyl-phenyl)-[ethoxy(phenyl)phosphoryl]methanone.

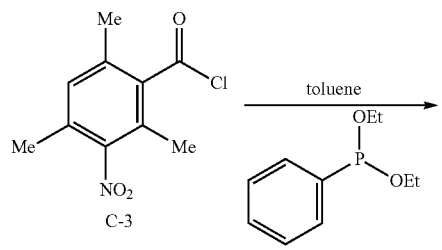

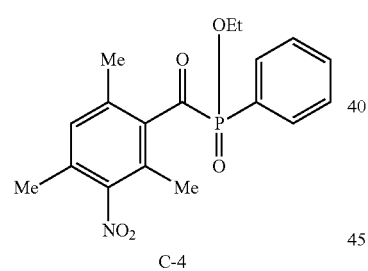

103.5 g (0.522 mol) diethyl-phenylphosphonite was dissolved in 500 ml toluene. The solution was heated to 80° C. 119 g (0.52 mol) of compound C-3 was dissolved in 250 ml toluene and added to the mixture over 15 minutes. The reaction was allowed to continue for three hours at 80° C. The reaction was allowed to cool down to room temperature and the mixture was extracted twice with 350 ml of saturated NaHCO$_3$-solution and twice with 400 ml brine. The organic fraction was isolated, dried over Na$_2$SO$_4$ and evaporated under reduced pressure. The crude compound C-4 was purified by preparative column chromatography on a Graceresolve RS80 column, using methylene chloride as eluent. 88 g of compound-C-4 (yield: 47%) was isolated. (TLC analysis on TLC Silica gel 60F$_{254}$ supplied by Merck, eluent methylene chloride/ethyl acetate 90/10: R$_f$: 0.49). The molecular mass was confirmed using the TLC-MS methodology described above.

Step 4: Synthesis of Compound C-5

The compound C-5 is (3-amino-2,4,6-trimethyl-phenyl)-[ethoxy(phenyl)phosphoryl]methanone

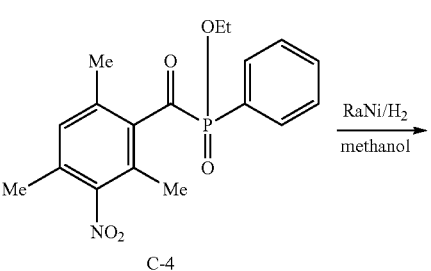

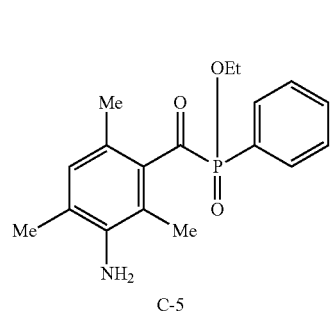

24.3 g (70 mmol) of compound C-4 was dissolved in 200 g methanol. 1 g of RaNi was washed three times with methanol and added to the reaction mixture. Compound C-4 was hydrogenated at 30° C. and 50 bar hydrogen pressure. Upon complete hydrogenation, the reaction mixture was allowed to cool down to room temperature and the RaNi was removed by filtration. The solvent was removed under reduced pressure and 21.6 g of compound C-5 was isolated (yield: 97.3%). Compound C-5 was used without further purification.

Step 5: Synthesis of Compound UREA-2

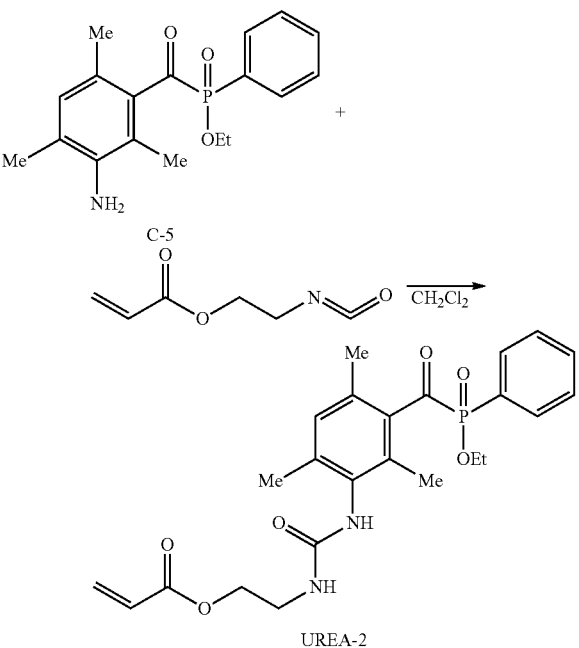

6.62 g (20 mmol) of compound C-5 as prepared in Example 1 was dissolved in 65 ml methylene chloride. A solution of 2.96 g (21 mmol) 2-acryloyloxyethyl acrylate was added and the reaction was allowed to continue for three hours at room temperature. An additional 1.48 g (10.5 mmol) 2-acryloyloxyethyl acrylate was added and the reaction was allowed to continue at room temperature for 16 hours. The solvent was removed under reduced pressure. UREA-2 was isolated by preparative column chromatography on a Prochrom LC80 column using Kromasil C18 100 Å 10 µm as stationary phase and methanol/0.2 M ammonium acetate 60/40 as eluent. 3.87 g (y: 41%) of UREA-2 was isolated (TLC analysis on Reveleris RP C18 TLC plates, supplied by Grace, methanol/1 M NaCl 60/40 as eluent, $R_f$: 0.16). UREA-2 was analyzed using $^1$H-NMR spectroscopy (DMSO d6, 50 µl trifluoroacetic acid in 0.7 ml DMSO d6).

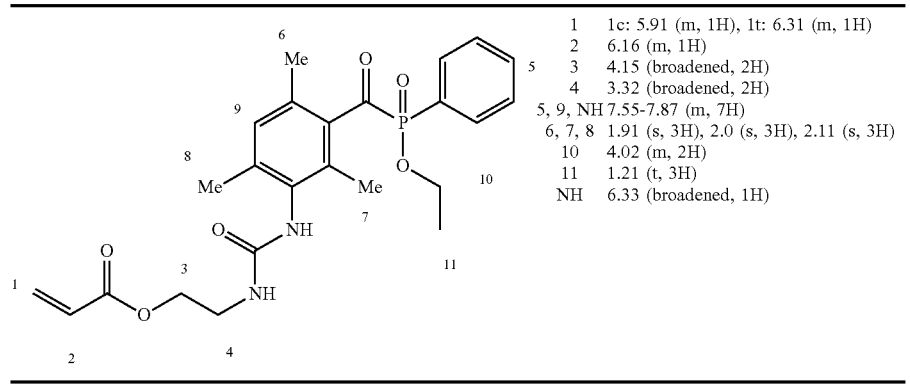

| | |
|---|---|
| 1 | 1c: 5.91 (m, 1H), 1t: 6.31 (m, 1H) |
| 2 | 6.16 (m, 1H) |
| 3 | 4.15 (broadened, 2H) |
| 4 | 3.32 (broadened, 2H) |
| 5, 9, NH | 7.55-7.87 (m, 7H) |
| 6, 7, 8 | 1.91 (s, 3H), 2.0 (s, 3H), 2.11 (s, 3H) |
| 10 | 4.02 (m, 2H) |
| 11 | 1.21 (t, 3H) |
| NH | 6.33 (broadened, 1H) |

Preparation of Radiation Curable Inkjet Inks

The radiation curable inkjet inks C-1 to C-3 and I-1 to I-3 were prepared according to Table 15. The same magenta dispersion DISP-M of Example 1 was used. The weight % (wt %) were based on the total weight of the UV curable inkjet inks.

TABLE 15

| wt % of | C-1 | C-2 | C-3 | I-1 | I-2 | I-3 |
|---|---|---|---|---|---|---|
| DISP-M | 26.56 | 26.56 | 26.56 | 26.56 | 26.56 | 26.56 |
| VEEA | 37.70 | | 36.70 | 32.70 | | 36.70 |
| NVC | | 37.70 | | | 32.70 | |
| MSOQ-1n4 | | | | 5.00 | 5.00 | 5.00 |
| TPO-L | 4.00 | 4.00 | | 4.00 | 4.00 | |
| UREA-2 | | | 5.00 | | | 5.00 |
| TX-1 | 20.00 | 20.00 | 20.00 | 20.00 | 20.00 | 20.00 |
| GAB | 10.00 | 10.00 | 10.00 | 10.00 | 10.00 | 10.00 |
| INHIB | 0.74 | 0.74 | 0.74 | 0.74 | 0.74 | 0.74 |
| C7500 | 1.00 | 1.00 | 1.00 | 1.00 | 1.00 | 1.00 |

Evaluation and Results

The viscosity and the surface tension of the radiation curable inkjet inks C-1 to C-3 and I-1 to I-3 was measured and is shown in Table 16,

TABLE 16

| Parameter | C-1 | C-2 | C-3 | I-1 | I-2 | I-3 |
|---|---|---|---|---|---|---|
| Viscosity (mPa·s) | 13 | 17 | 15 | 14 | 19 | 16 |

TABLE 16-continued

| Parameter | C-1 | C-2 | C-3 | I-1 | I-2 | I-3 |
|---|---|---|---|---|---|---|
| Surface Tension (mN/m) | 28 | 29 | 28 | 28 | 29 | 28 |

The radiation curable inkjet inks C-1 to C-3 and I-1 to I-3 were coated on a PET175 substrate using a bar coater and a 10 µm wired bar. All coated samples were cured using a Fusion DRSE-120 conveyer, equipped with a Fusion VPS/1600 lamp (D-bulb). The samples were cured three times at a belt speed of 20 m/min at full power of the lamp. All samples were fully cured.

The UV cured samples were evaluated for smell by seven persons resulting in an averaged smell score as shown in Table 17.

TALE 17

| UV Cured Sample | Averaged smell score |
|---|---|
| C-1 | 2 |
| C-2 | 4 |
| C-3 | 2 |
| I-1 | 2 |
| I-2 | 3 |
| I-3 | 2 |

From Table 17, it becomes apparent that all radiation curable inkjet inks according to invention I-1 to I-3 had an averaged smell score of 3 or less.

The radiation curable inkjet inks C-1 to C-3 and I-1 to I-3 were used to print an identical image of 20 cm$^2$ on an aluminium substrate of 25 cm$^2$ with a Anapurna™ H2050i LED inkjet system available from AGFA NV.

The printed samples were then tested on formaldehyde emission and acetaldehyde emission with the above described analytical procedures. The analytical results are given in Table 18.

TABLE 18

| µg/m$^2$ of: | C-1 | C-2 | C-3 | I-1 | I-2 | I-3 |
|---|---|---|---|---|---|---|
| Formaldehyde | 824 | 988 | 630 | 1 | 15 | 7 |
| Acetaldehyde | 2191 | 10222 | 2026 | 1043 | 721 | 847 |

The results in Table 18 clearly show that the radiation curable inkjet inks I-1 to I-3 in accordance with the invention produces far less formaldehyde and acetaldehyde than the comparative radiation curable inkjet inks C-1 to C-3. It is also observed that the use of an acyl phosphine oxide photoinitiator having a polymerizable group on the acyl group further reduces the aldehyde emission compared to the same acyl phosphine oxide photoinitiator lacking a polymerizable group on the acyl group.

The invention claimed is:

1. A radiation curable inkjet ink comprising:
    a) at least one compound selected from the group consisting of a polymerizable compound including a vinylether group or a vinylamide group, an amine synergist including an alkanolamine group or a dimethyl benzoate group, and a Norrish Type II photoinitiator including a photoinitiating moiety selected from the group consisting of a thioxanthone group, a benzophenone group, a ketocoumarin group, and a camphorquinone group; and
    b) a singlet oxygen quencher including at least one amino-thioether group selected from the group consisting of:
    1) a monofunctional singlet oxygen quencher according to Formula (IV):

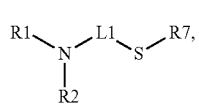

Formula (IV)

wherein
    L1 represents a divalent linking group positioning S and N in a 1 to 2 to a 1 to 4 position;
    R1 and R2 are each independently selected from the group consisting of a methyl group, a $C_2$-$C_6$-alkyl group, a $C_2$-$C_6$-alkenyl group, a $C_2$-$C_6$-alkynyl group and a $C_7$-$C_{12}$-aralkyl group, wherein any of said $C_2$-$C_6$-alkyl group, $C_2$-$C_6$-alkenyl group, $C_2$-$C_6$-alkynyl group and $C_7$-$C_{12}$-aralkyl group may be interrupted by at least one hetero-atom selected from the group consisting of a nitrogen, an oxygen and a sulphur; and is optionally functionalized with a functional group selected from the group consisting of an ester, an amide, a ketone, an aldehyde, a sulfone, a sulfonate ester and a phosphonate; and
    R7 is selected from the group consisting of a methyl group, $C_2$-$C_{20}$-alkyl group, a $C_2$-$C_{20}$-alkenyl group, a $C_2$-$C_{20}$-alkynyl group and a $C_7$-$C_{20}$-aralkyl group, wherein any of said $C_2$-$C_{20}$-alkyl group, $C_2$-$C_{20}$-alkenyl group, $C_2$-$C_{20}$-alkynyl group and $C_7$-$C_{20}$-aralkyl group may be interrupted by at least one hetero-atom selected from the group consisting of a nitrogen, an oxygen and a sulphur or may be optionally functionalized with a functional group selected from the group consisting of an ester group, an amide group, a ketone group, an aldehyde group, a sulfone group, a sulfonate ester group and a phosphonate group;
    2) a monofunctional singlet oxygen quencher according to Formula (V):

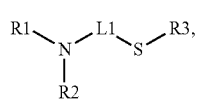

Formula (V)

wherein
    L1 represents a divalent linking group positioning S and N in a 1 to 2 to a 1 to 4 position;
    R1 and R2 are each independently selected from the group consisting of a methyl group, a $C_2$-$C_6$-alkyl group, a $C_2$-$C_6$-alkenyl group, a $C_2$-$C_6$-alkynyl group and a $C_7$-$C_{12}$-aralkyl group, wherein any of said $C_2$-$C_6$-alkyl group, $C_2$-$C_6$-alkenyl group, $C_2$-$C_6$-alkynyl group and $C_7$-$C_{12}$-aralkyl group may be interrupted by at least one hetero-atom selected from the group consisting of a nitrogen, an oxygen and a sulphur; and is optionally functionalized with a functional group selected from the group consisting of an ester, an amide, a ketone, an aldehyde, a sulfone, a sulfonate ester and a phosphonate; and
    R3 represents a group selected from the group consisting of a $C_1$-$C_{20}$-alkyl group, a $C_2$-$C_{20}$-alkyl group which is interrupted by one oxygen atom and/or an ester group, a $C_2$-$C_{20}$-alkenyl group, a $C_2$-$C_{20}$-alkenyl group which is interrupted by one or more oxygen atoms and/or ester groups, a $C_2$-$C_{20}$-alkynyl group, a $C_2$-$C_{20}$-alkynyl group which is interrupted by one or more oxygen atom and/or ester groups, a $C_7$-$C_{20}$-aralkyl group, and one or more free radical polymerizable functional groups selected from the group consisting of an acrylate, a methacrylate, an acrylamide and a methacrylamide;
    3) a monofunctional singlet oxygen quencher according to Formula (VI):

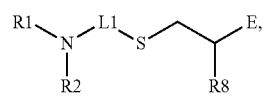

Formula (VI)

wherein
    E is selected from the group consisting of an ester group and an amide group;
    R8 is selected from the group consisting of a hydrogen and a methyl group;
    L1 represents a divalent linking group positioning S and N in a 1 to 2 to a 1 to 4 position; and
    R1 and R2 are each independently selected from the group consisting of a methyl group, a $C_2$-$C_6$-alkyl group, a $C_2$-$C_6$-alkenyl group, a $C_2$-$C_6$-alkynyl group and a $C_7$-$C_{12}$-aralkyl group, wherein any of said $C_2$-$C_6$-alkyl group, $C_2$-$C_6$-alkenyl group, $C_2$-$C_6$-alkynyl group and $C_7$-$C_{12}$-aralkyl group may be interrupted by at least one hetero-atom selected from the group consisting of a nitrogen, an oxygen and a sulphur; and is optionally functionalized with a functional group selected from the group consisting of an ester, an amide, a ketone, an aldehyde, a sulfone, a sulfonate ester and a phosphonate;
    4) a difunctional singlet oxygen quencher according to Formula (VII):

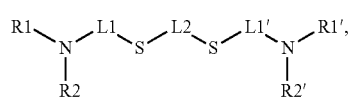

Formula (VII)

wherein
    L1 and L1' each independently represent a divalent linking group positioning S and N in a 1 to 2 to a 1 to 4 position;
    R1, R2, R1' and R2' are each independently selected from the group consisting of $C_1$-$C_6$-alkyl group, a $C_2$-$C_6$-alkenyl group, a $C_2$-$C_6$-alkynyl group and a $C_7$-$C_{12}$-aralkyl group wherein any of the $C_1$-$C_6$-alkyl group, the $C_2$-$C_6$-alkenyl group, the $C_2$-$C_6$-alkynyl group and the $C_7$-$C_{12}$-aralkyl group may be interrupted by at least one hetero-atom selected from the group consisting of a nitrogen, an oxygen and a sulphur, or may be optionally functionalized with a functional group selected from the group consisting of an ester group, an amide group, a ketone group, an aldehyde group, a sulfone group, a sulfonate ester group and a phosphonate group; and L2 represents a divalent linking group selected from the group consisting of an alkylene group, an alkenylene group, an alkynylene group, an aralkylene group, all of them comprising no more than 20 carbon atoms and optionally interrupted by a hetero-atom selected from the group of an oxygen, a sulphur or a nitrogen and/or a functional group selected from the group consisting of an ester group, an amide group, and an oligo-ether group selected from the group consisting of an oligo-ethylene oxide, an oligo-propylene oxide and an oligo-tetramethylene oxide or combinations thereof; and 5) a singlet oxygen quencher selected from the group consisting of:

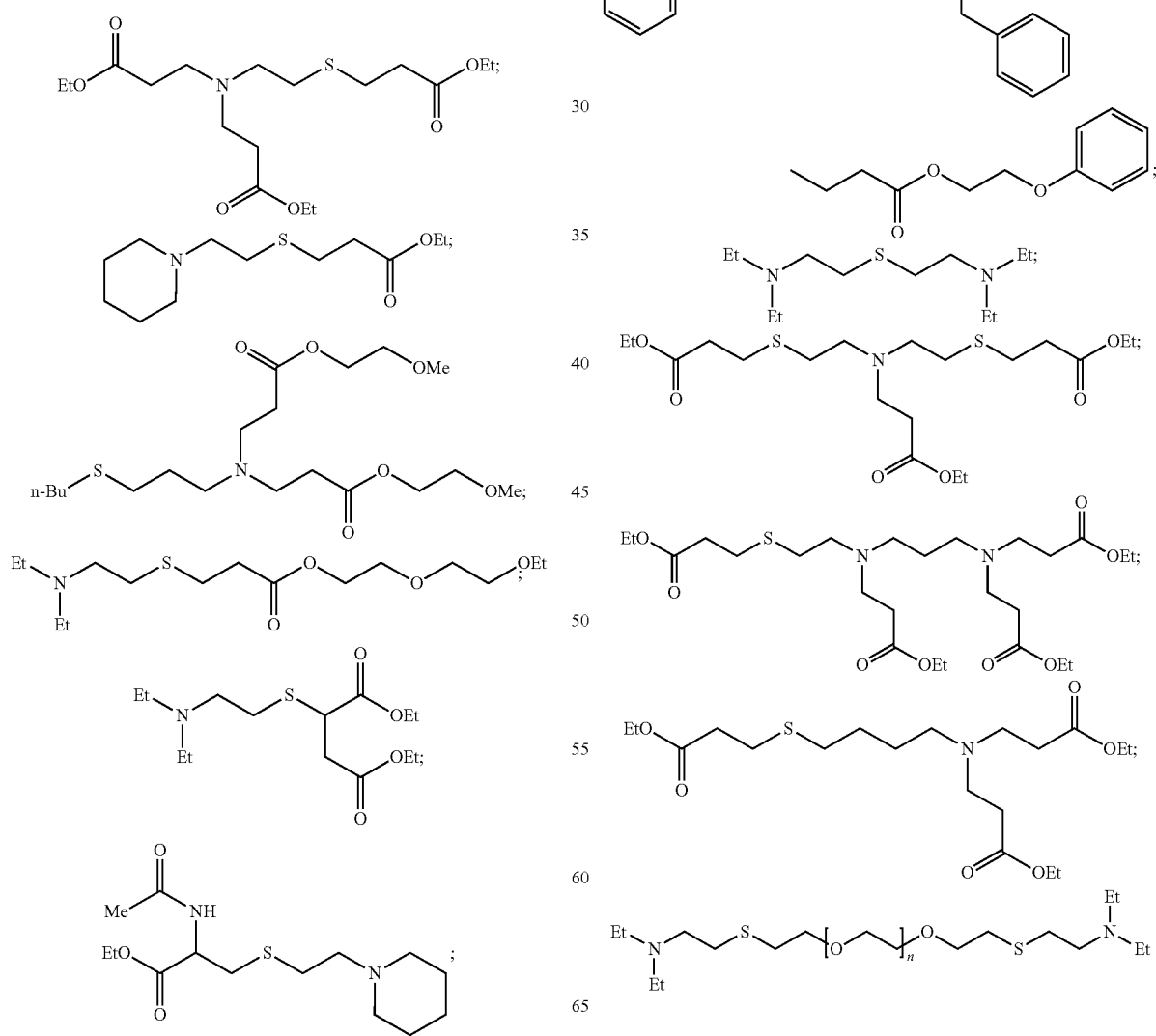

with n representing an integer of 2 to 20 on average;

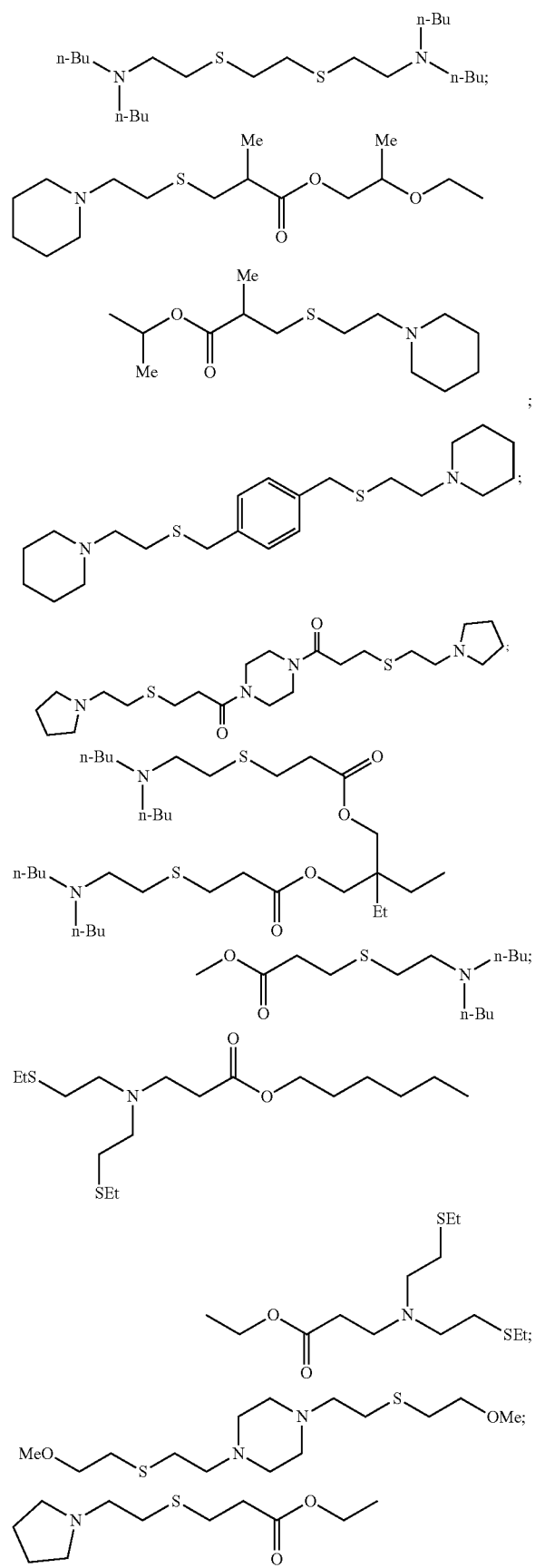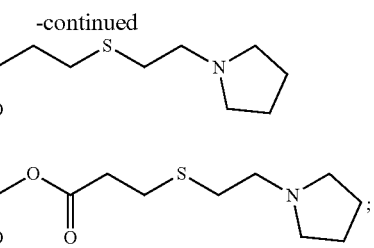

-continued

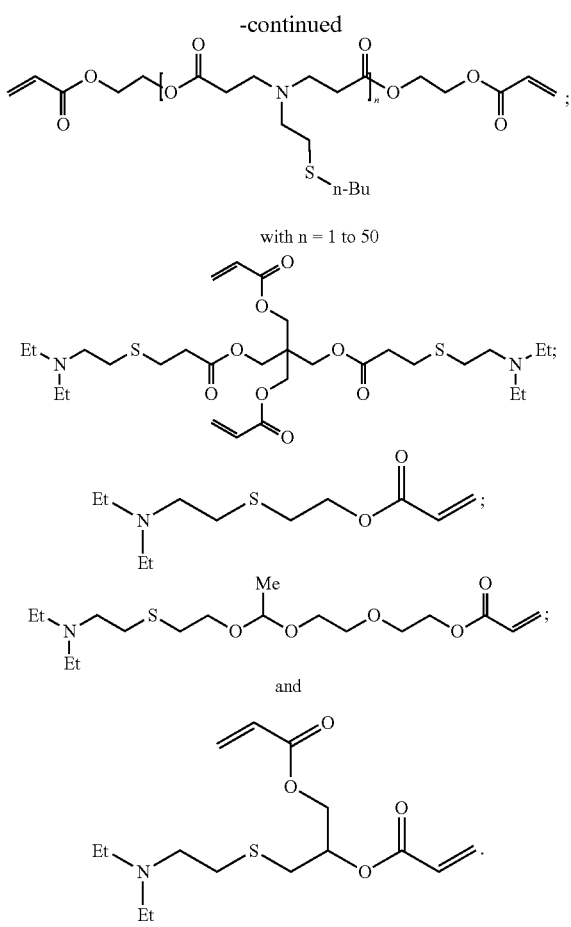

with n = 1 to 50

2. The radiation curable inkjet ink of claim 1, wherein L1 in the singlet oxygen quencher according to any one of Formula (IV) to (VI) represents an ethylene group, a propylene group, or a butylene group.

3. The radiation curable inkjet ink of claim 1, wherein in the singlet oxygen quencher according to Formula (IV) or (VI), R1 and R2 are independently selected from the group consisting of a $C_1$-$C_6$-alkyl group, a $C_2$-$C_6$-alkyl group which is interrupted by one oxygen atom and/or an ester group, a $C_2$-$C_6$-alkenyl group, a $C_2$-$C_6$-alkenyl group which is interrupted by one oxygen atom and/or an ester group, a $C_2$-$C_6$-alkynyl group, a $C_2$-$C_6$-alkynyl group which is interrupted by one oxygen atom and/or an ester group, and a $C_7$-$C_{12}$-aralkyl group.

4. The radiation curable inkjet ink of claim 2, wherein in the singlet oxygen quencher according to Formula (IV) or (VI), R1 and R2 are independently selected from the group consisting of a $C_1$-$C_6$-alkyl group, a $C_2$-$C_6$-alkyl group which is interrupted by one oxygen atom and/or an ester group, a $C_2$-$C_6$-alkenyl group, a $C_2$-$C_6$-alkenyl group which is interrupted by one oxygen atom and/or an ester group, a $C_2$-$C_6$-alkynyl group, a $C_2$-$C_6$-alkynyl group which is interrupted by one oxygen atom and/or an ester group, and a $C_7$-$C_{12}$-aralkyl group.

5. The radiation curable inkjet ink of claim 1, wherein the singlet oxygen quencher contains at least one free radical polymerizable functional group selected from the group consisting of an acrylate, a methacrylate, an acrylamide, and a methacrylamide.

6. The radiation curable inkjet ink of claim 1, wherein the polymerizable compound containing a vinylether group is a vinyl ether acrylate compound.

7. The radiation curable inkjet ink of claim 6, wherein the vinyl ether acrylate compound is 2-(2-vinyloxyethoxy)ethyl acrylate.

8. The radiation curable inkjet ink of claim 1, wherein the polymerizable compound containing a vinylamide group is N-vinylcaprolactam.

9. The radiation curable inkjet ink of claim 1, further containing an acylphosphine oxide photoinitiator or an α-hydroxy ketone photoinitiator.

10. The radiation curable inkjet ink of claim 9, wherein the one or more acyl groups of the acylphosphine oxide photoinitiator or α-hydroxy ketone photoinitiator are connected to a polymer or to a polymerizable group.

11. A radiation curable inkjet ink set including one or more radiation curable inkjet inks according to claim 1.

12. An indoor decorative article including a cured layer of one or more radiation curable inkjet inks according to claim 1, wherein the indoor decorative article is selected from the group consisting of decorative panels, furniture, wallpaper, doors, and textile fabrics.

13. An inkjet printing method including the steps of:
printing one or more radiation curable inks according to claim 1 on a substrate; and
UV curing the one or more curable inks on the substrate.

14. The inkjet printing method of claim 13, wherein the UV curing is performed by UV LEDs having an emission wavelength larger than 360 nm.

15. A method of manufacturing indoor decorative articles, the method comprising the inkjet printing method according to claim 13.

16. A method of manufacturing indoor decorative articles, the method comprising the inkjet printing method according to claim 14.

17. The method of manufacturing indoor decorative articles of claim 15, wherein the indoor decorative article is selected from the group consisting of decorative panels, furniture, wallpaper, doors, leather articles, and textile fabrics.

18. The method of manufacturing indoor decorative articles of claim 16, wherein the indoor decorative article is selected from the group consisting of decorative panels, furniture, wallpaper, doors, leather articles, and textile fabrics.

* * * * *